(12) United States Patent
Klinger

(10) Patent No.: US 7,923,215 B2
(45) Date of Patent: *Apr. 12, 2011

(54) PROCESS FOR THE MEASUREMENT OF THE POTENCY OF GLATIRAMER ACETATE

(75) Inventor: Ety Klinger, Tel Aviv (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 37 days.

This patent is subject to a terminal disclaimer.

(21) Appl. No.: 12/231,081

(22) Filed: Aug. 28, 2008

(65) Prior Publication Data

US 2009/0053253 A1 Feb. 26, 2009

Related U.S. Application Data

(63) Continuation of application No. 10/313,726, filed on Dec. 4, 2002, now Pat. No. 7,429,374.

(60) Provisional application No. 60/338,767, filed on Dec. 4, 2001.

(51) Int. Cl.
G01N 33/53 (2006.01)

(52) U.S. Cl. .................................................. 435/7.24

(58) Field of Classification Search .................. None
See application file for complete search history.

(56) References Cited

U.S. PATENT DOCUMENTS

| | | | |
|---|---|---|---|
| 3,849,550 | A | 11/1974 | Teitelbaum et al. |
| 3,991,210 | A | 11/1976 | Shea |
| 4,129,666 | A | 12/1978 | Wizerkaniuk |
| 4,339,431 | A | 7/1982 | Gaffar |
| 4,594,409 | A | 6/1986 | Hayashi et al. |
| 5,204,099 | A | 4/1993 | Barbier et al. |
| 5,554,372 | A | 9/1996 | Hunter et al. |
| 5,583,031 | A | 12/1996 | Stern |
| 5,591,629 | A | 1/1997 | Rodriguez et al. |
| 5,623,052 | A | 4/1997 | McLean et al. |
| 5,627,206 | A | 5/1997 | Hupe et al. |
| 5,668,117 | A | 9/1997 | Shapiro |
| 5,716,946 | A | 2/1998 | DeLuca et al. |
| 5,719,296 | A | 2/1998 | Acton, III et al. |
| 5,734,023 | A | 3/1998 | Nag et al. |
| 5,800,808 | A | 9/1998 | Konfino et al. |
| 5,858,964 | A | 1/1999 | Aharoni et al. |
| 5,886,156 | A | 3/1999 | McLean et al. |
| 5,958,972 | A | 9/1999 | Hupe et al. |
| 5,965,600 | A | 10/1999 | Sato et al. |
| 5,981,589 | A | 11/1999 | Konfino et al. |
| 6,024,981 | A | 2/2000 | Khankari et al. |
| 6,048,898 | A | 4/2000 | Konfino et al. |
| 6,054,430 | A | 4/2000 | Konfino et al. |
| 6,162,800 | A | 12/2000 | Dolle et al. |
| 6,214,791 | B1 | 4/2001 | Arnon et al. |
| 6,342,476 | B1 | 1/2002 | Konfino et al. |
| 6,362,161 | B1 | 3/2002 | Konfino et al. |
| 6,369,099 | B1 | 4/2002 | DeLuca et al. |
| 6,514,938 | B1 | 2/2003 | Gad et al. |
| 6,620,847 | B2 | 9/2003 | Konfino et al. |
| 6,800,285 | B2 | 10/2004 | Rodriguez et al. |
| 6,800,287 | B2 | 10/2004 | Gad et al. |
| 6,844,314 | B2 | 1/2005 | Eisenbach-Schwartz |
| 6,855,270 | B2 | 2/2005 | Mumper et al. |
| 6,939,539 | B2 | 9/2005 | Konfino et al. |
| 7,022,663 | B2 | 4/2006 | Gilbert et al. |
| 7,033,582 | B2 | 4/2006 | Yong et al. |
| 7,074,580 | B2 | 7/2006 | Gad et al. |
| 7,163,802 | B2 | 1/2007 | Gad et al. |
| 7,199,098 | B2 | 4/2007 | Konfino et al. |
| 7,279,172 | B2 | 10/2007 | Aharoni et al. |
| 7,407,936 | B2 | 8/2008 | Eisenbach-Schwartz et al. |
| 7,425,332 | B2 | 9/2008 | Aharoni et al. |
| 7,429,374 | B2 * | 9/2008 | Klinger .................. 424/9.2 |
| 7,495,072 | B2 | 2/2009 | Dolitzky et al. |
| 7,566,767 | B2 | 7/2009 | Strominger et al. |
| 2002/0037848 | A1 | 3/2002 | Eisenbach-Schwartz et al. |
| 2002/0107388 | A1 | 8/2002 | Vandenbark |
| 2003/0170729 | A1 | 9/2003 | Klinger |
| 2004/0006022 | A1 | 1/2004 | Strominger et al. |
| 2005/0170004 | A1 | 8/2005 | Rosenberger et al. |
| 2006/0052586 | A1 | 3/2006 | Dolitzky et al. |
| 2006/0122113 | A1 | 6/2006 | Pinchasi et al. |
| 2006/0172942 | A1 | 8/2006 | Dolitzky |
| 2006/0240463 | A1 | 10/2006 | Lancet |
| 2006/0264354 | A1 | 11/2006 | Aharoni |
| 2007/0021324 | A1 | 1/2007 | Dolitzky |
| 2007/0021341 | A1 | 1/2007 | Sela et al. |
| 2007/0048794 | A1 | 3/2007 | Gad et al. |

(Continued)

FOREIGN PATENT DOCUMENTS

AU 2002353059 10/2008

(Continued)

OTHER PUBLICATIONS

U.S. Appl. No. 09/359,099, filed Jul. 22, 1999, Strominger et al.
Abramsky, et al., "Effect of a Synthetic Polypeptide (COP-1) on Patients with Multiple Sclerosis and with Acute Disseminated Encephalomyelitis", J. Neurol. Sci., 1977, 31, 433-438.
Aharoni, R. et al., (1993) "T Suppressor Hybridomas and Interleukin-2-Dependent Lines Induced by Copolymer I or by Spinal Cord Homogenate Down-Regulate Experimental Allergic Encephalomyelitis", Eur. J. Immunol., vol. 23, pp. 17-25.
Aharoni, et al., "Studies on the Mechanism and Specificity of the Effect of the Synthetic Random Copolymer GLAT on Graft-versus-Host Disease", Immunol. Letters, 1997, 58, 79-87.
Aharoni (1997) "Copolymer 1 Induces T Cells of the T Helper Type 2 that Crossreact with Myelin Basic Protein and Suppress Experimental Autoimmune Encephalomyelitis", Proc. Natl. Acad. Sci. USA, vol. 94, pp. 10821-10826.
Aharoni, et al., "Cop 1 Specific Suppressor Cells Inhibit Experimental Allergic Encephalomyelitis Induced by Either Mouse Spinal Cord Homogenate or Proteolipid Protein Peptide 139-151", Neurology, 1997, vol. 48, No. 3, A422.

(Continued)

Primary Examiner — David A Saunders
(74) Attorney, Agent, or Firm — John P. White; Cooper & Dunham LLP

(57) ABSTRACT

The subject invention provides a process for measuring the relative potency of a test batch of glatiramer acetate. In addition, the subject invention provides a process for preparing a batch of glatiramer acetate as acceptable for pharmaceutical use.

30 Claims, 17 Drawing Sheets

U.S. PATENT DOCUMENTS

| | | | |
|---|---|---|---|
| 2007/0054857 A1 | 3/2007 | Pinchasi et al. | |
| 2007/0059798 A1 | 3/2007 | Gad et al. | |
| 2007/0173442 A1 | 7/2007 | Vollmer et al. | |

FOREIGN PATENT DOCUMENTS

| | | |
|---|---|---|
| CA | 2469393 | 5/2010 |
| DK | DE3930733 | 3/1991 |
| EP | 0383620 A2 | 8/1990 |
| EP | 0359783 B1 | 11/1995 |
| EP | 1292279 | 3/2003 |
| EP | 0378246 A1 | 6/2003 |
| EP | 1459065 | 7/2010 |
| NZ | 254496 | 8/1990 |
| NZ | 336690 | 1/1998 |
| RU | 1690368 | 8/1995 |
| RU | 1469826 | 11/1995 |
| SU | 1182051 | 9/1985 |
| SU | 1664845 | 6/1991 |
| WO | WO 88/10120 | 12/1988 |
| WO | WO 92/02543 | 2/1992 |
| WO | WO 94/03484 | 2/1994 |
| WO | WO 94/26774 | 11/1994 |
| WO | WO 95/26980 | 10/1995 |
| WO | WO 95/31990 | 11/1995 |
| WO | WO 95/31997 | 11/1995 |
| WO | WO 95/33475 | 12/1995 |
| WO | WO 98/30227 | 7/1998 |
| WO | WO 00/05250 | 2/2000 |
| WO | WO0005249 | 2/2000 |
| WO | WO 00/18794 | 4/2000 |
| WO | WO 00/20010 | 4/2000 |
| WO | WO 00/27417 | 5/2000 |
| WO | WO0152878 | 7/2001 |
| WO | WO0160392 | 8/2001 |
| WO | WO0185797 | 11/2001 |
| WO | WO0193828 | 12/2001 |
| WO | WO0193893 | 12/2001 |
| WO | WO0197846 | 12/2001 |
| WO | WO02076503 | 10/2002 |
| WO | WO03048735 | 6/2003 |
| WO | WO2004043995 | 5/2004 |
| WO | WO2005041933 | 5/2005 |
| WO | WO2006050122 | 5/2006 |
| WO | WO 2006/116602 | 11/2006 |
| WO | WO2008006026 | 1/2008 |
| ZA | SA980214 | 9/1999 |

OTHER PUBLICATIONS

Aharoni, R. et al., (1998) "Bystander Suppression of Experimental Autoimmune Encephalomyelitis by T cell Lines and Clones of the Th2 Type Induced by Copolymer 1", Journal of Neuroimmunology, vol. 91, No. 1-2, pp. 135-146.

Aharoni, et al., "Copolymer 1 Inhibits Manifestations of Graft Rejection", Transplantation, 2001, vol. 72, No. 4, 598-605.

Alvord, et al., "Myelin Basic Protein Treatment of Experimental Allergic Encephalomyelitis in Monkeys", Ann. Neurol., 1979, 6, 469-473.

Arnon, et al., "Suppression of Experimental Allergic Encephalomyelitis by a Synthetic Copolymer Immunological Cross Reactive with Basic Encephalitogen", Israel J. Med. Sci., 1972, 8, 1759-1760 (Abstract).

Arnon, et al., "Suppression of EAE in Baboons by a Synthetic Polymer of Amino Acids", Neurol., 1978, 28, 336 (Abstract).

Arnon, "A Synthetic Copolymer of Amino Acids in a Clinical Trial for MS Therapy", Progress in Multiple Sclerosis Research (Bauer, Ritter, eds., Springer Verlag New York, 1980) 416-418.

Arnon, et al., "Desensitization of Experimental Allergic Encephalomyelitis with Synthetic Peptide Analogues", The Suppression of Experimental Allergic Encephalomyelitis and Multiple Sclerosis (Academic Press, New York, 1980) 105-107.

Arnon, "Experimental Allergic Encephalomyelitis—Susceptibility and Suppression", Immunological Rev., 1981, 55, 5-30.

Arnon, et al., "Suppression of Demyelinating Diseases by Synthetic Copolymers", A Multidisciplinary Approach to Myelin Disease (G. Serlupi Crescenzi, ed., Plenum Publishing Corp., 1988) 243-250.

Arnon, et al., "Suppression of Experimental Allergic Encephalomyelitis by Cop-1—Relevance to Multiple Sclerosis", Israel J. Med. Sci., 1989, 25, 686-689.

Arnon, et al., "On the Existence of Suppressor Cells", Int. Arch. Allergy Immunol., 1993, 100, 2-7.

Arnon, et al., "Immunomodulation of Experimental Allergic Encephalomyelitis", Israel J. Med. Sci., 1993, 29, 175-181.

Arnon, et al., "Immunospecific Drug Design—Prospects for Treatment of Autoimmune Disease", Therapeutic Immunol., 1994, 1, 65-70.

Asakura and Rodriguez, "A Unique Population of Circulating Autoantibodies Promotes Central Nervous System Remyelination", Multiple Sclerosis, 1998, 4: 217-221).

Asakura, et al., "Targeting of IgMκ Antibodies to Oligodendrocytes Promotes CNS Remyelination", J. Neurosci., 1998, 18(19): 7700-7708.

Babu, et al., "Reevaluation of Response Patterns of Nonresponder Mice to GlPhe Polymers", Immunogen., 1983, 18(1): 97-100 (Abstract).

Babu, et al., "Ir Gene Control of T and B Cell Responses to Determinants in (Glu Lys Ala) Terpolymer", J. Immunogenet., 1984, 11 (3-4): 251-254 (Abstract).

Bansil, et al., "Multiple Sclerosis: Pathogenesis and Treatment", Seminars in Neurol., Jun. 1994, 14(2), 146-153.

Batchelor, et al., "Hydralazine-Induced Systemic Lupus Erythematosus: Influence of HLA-DR and Sex on Susceptibility", Lancet, 1980, 1(8178), 1107-9.

Baumhefner, et al., "Copolymer 1 as Therapy for Multiple Sclerosis: The Cons", Neurol., 1988, 38(Suppl. 2), 69-71.

Baxevanis, et al., "Genetic Control of T-Cell Proliferative Responses to Poly (Glu40Ala60) and Poly (Glu51Lys34Tyr15): Subregion-Specific Inhibition of the Responses with Monoclonal Ia Antibodies", Immunogenetics, 1980, 11: 617-628.

Ben-Nun, et al., "The Autoimmune Reactivity to Myelin Oligodendrocyte Glycoprotein (MOG) in Multiple Sclerosis is Potentially Pathogenic: Effect of Copolymer 1 on MOG-induced Disease", J. Neurol., 1996, 243(Suppl. 1), S14-S22.

Bieber, et al., "Antibody-Mediated Remyelination: Relevance to Multiple Sclerosis", Multiple Sclerosis, 2000, 6: (Suppl.2) S1-S5.

Bieber, et al., "Humoral Autoimmunity as a Mediator of CNS Repair", Trends in Neurosci., 2001, 24(11): S39-S44.

Bodanszky, M. Principles of Peptide Synthesis Springer-Verlag, Berlin, Heidelberg, New York, Tokyo, 1984, pp. 118-229.

Bornstein, et al., "Treatment of Multiple Sclerosis with a Synthetic Polypeptide: Preliminary Results", Ann. Neurol., 1980, 8, 117 (Abstract).

Bornstein, et al., "Treatment of Multiple Sclerosis with a Synthetic Polypeptide: Preliminary Results", Trans. Am. Neurol. Assoc., 1980, 105, 348-350.

Bornstein, et al., "Multiple Sclerosis: Trial of a Synthetic Polypeptide", Ann. Neurol., 1982, 11, 317-319.

Bornstein, et al., "Clinical Trials of Copolymer 1 in Multiple Sclerosis", Ann. N.Y. Acad. Sci. (USA), 1984, 366-372.

Bornstein, et al., "Clinical Trials of a Synthetic Polypeptide (Copolymer 1) for the Treatment of Multiple Sclerosis" in Gonsett et al., Immunological and Clinical Aspects of Multiple Sclerosis (MTP Press, The Hague, 1984) 144-150.

Bornstein, et al., "Multiple Sclerosis: Clinical Trials of a Synthetic Polypeptide, Copolymer 1", Neurol., 1985, 35(Suppl. 1), 103 (Abstract).

Bornstein, "Cop 1 May be Beneficial for Patients with Exacerbating-remitting Form of Multiple Sclerosis", Adv. Ther. (USA), 1987, 4, 206 (Abstract).

Bornstein, et al., "A Pilot Trial of Cop 1 in Exacerbating-remitting Multiple Sclerosis", New Eng. J. Med., 1987, 317(7), 408-414.

Bornstein, et al., "Clinical Experience with COP-1 in Multiple Sclerosis", Neurol., 1988, 38(Suppl. 2), 66-69.

Bornstein, et al., "Pilot Trial of COP-1 in Chronic Progressive Multiple Sclerosis: Preliminary Report", from The International Multiple Sclerosis Conference: An Update on Multiple Sclerosis, Roma (Italy), Sep. 15-17, 1988, in Elsevier Science Publisher, 1989, 225-232.

Bornstein, et al., "Rationale for Immunomodulating Therapies of Multiple Sclerosis", Neurology, 1988 38(Suppl 2) 80-81.

Bornstein, et al., "Clinical Trials of Cop 1 in Multiple Sclerosis", Handbook of Multiple Sclerosis (S.D. Cook Marcel Rekker, ed., 1990) 469-480.

Bornstein, et al., "A Placebo-controlled, Double-blind, Randomized Two-center, Pilot Trial of Cop 1 in Chronic Progressive Multiple Sclerosis", Neurol., 1991, 41, 533-539.

Bornstein, et al., "Treatment of Multiple Sclerosis with Copolymer 1" in Treatment of Multiple Scleorsis: Trial Design, Results and Future Perspectives (Rudick R.A. & Goodkin D.E., eds., Springer Verlag, London, 1992) 173-198.

Bornstein, M., Clinical Experience: Hopeful Prospects In Multiple Sclerosis, Hospital Practice, 1992, vol. 27, No. 5, pp. 135-158.

Brosnan, et al., "The Response of Normal Human Lymphocytes to Copolymer 1", J. Neuropath. Exp. Neurol., 1983, 42, 356 (Abstract).

Brosnan, et al., "Copolymer 1: Effect on Normal Human Lymphocytes", Ann. N.Y. Acad. Sci. (USA), 1984, 436, 498-499.

Brosnan, et al., "Immunogenic Potentials of Copolymer 1 in Normal Human Lymphocytes", Neurol., 1985, 35, 1754-1759.

Burns, et al., "Human Cellular Immune Response in Vitro to Copolymer 1 and Myelin Basic Protein (MBP)", Neurol., 1985, 35 (Suppl. 1), 170 (Abstract).

Burns, et al., "Human Cellular Immune Response to Copolymer 1 and Myelin Basic Protein", Neurol., 1986, 36, 92-94.

Burns, et al., "Failure of Copolymer 1 to Inhibit the Human T-cell Response to Myelin Basic Protein", Neurol., 1991, 41, 1317-1319.

Carter, et al., "Newer Drug Therapies for Multiple Sclerosis", Drug Therapy, 1990, 31-32, 37-39, 42-43.

Cazzato, et al., "Treatment of Multiple Sclerosis. The Present and the Future. Study Group on Diagnosis and Therapy of Multiple Sclerosis", Database Medline on STN, Instituto do Clinica Neurologica, Universita, Trieste, Italy: Medline AN: 2000060325, Recent Progressi in Medicina. Oct. 1999, 90(10), 538-544 (Abstract).

Clinical Trial Protocol No. 9001, Teva Pharmaceutical Industries, Ltd., first patient enrolled Oct. 23, 1991.

Clinical Trial Protocol No. 9002, Lemmon Co. and Teva Pharmaceutical Industries, Ltd., first patient enrolled Jun. 17, 1993.

Cohen, "Fundamental Immunology", Systemic Autoimmunity, 4th Ed., 1999, 1067-1088.

Cotton, "Options for Multiple Sclerosis Therapy", J.A.M.A. Medical News & Perspectives, 1994, 272(18), 1393.

Deeb, et al., "Comparision of Freund's and Ribi Adjuvants for Inducing Antibodies to the Synthetic Antigen (TG)-AL in Rabbits", J. Immunol. Methods, 1992, 152(1): 105-113 (Abstract).

De Kruyff, et al., "Analysis of T Cell Responses to Poly-L (GluLys) at the Clonal Level. I. Presence of Responsive Clones in Nonresponder Mice", Eur. J. Immunol., 1987, 17 (8): 1115-1120 (Abstract).

Dorling, et al., "Prospects for Xenografting", Curr. Opinions Immunol., 1994, 6, 765-769.

Duda, et al., (2000) "Human and Murine CD4 T Cell Reactivity to a Complex Antigen: Recognition of the Synthetic Random Polypeptide Glatiramer Acetate", Journal of Immunology, vol. 165, No. 12, pp. 7300-7307.

Durelli, "Immunotherapeutics of Multiple Sclerosis", Instituto di Clinica delle Malattie del Sistema Nervoso Universita di Torino, 467-475.

Falo, et al., "Analysis of Antigen Presentation by Metabolically Inactive Accessory Cells and Their Isolated Membranes", Proc. Natl. Acad. Sci. USA, 1985, 82(19): 6647-6651 (Abstract).

Fatma et al., "HLA-DRB 1 association in Turkish psoriasis vulgaris patients", Swiss Med. Wkly., 2003, 133:541-543.

Ferrara, et al., "Graft-Versus-Host Disease", New Eng. J. Med., 1991, 324, 667-674.

Francis, "The Current Therapy of Multiple Sclerosis", J. Clin. Pharmacy and Therapeutics, 1993, 18, 77-84.

Fridkis-Hareli, et al., "Copolymer 1 Displaces MBP, PLP and MOG, but Can Not be Displaced by these Antigens from the MHC Class II Binding Site", Department of Chemical Immunology, The Weizmann Institute of Science, 1994 (Abstract).

Fridkis-Hareli, et al., "Direct Binding of Myelin Basic Protein and Synthetic Copolymer 1 to Class II Major Histocompatibility Complex Molecules on Living Antigen-Presenting Cells—Specificity and Promiscuity", Proc. Natl. Acad. Sci. USA, 1994, 91, 4872-4876.

Fridkis-Hareli, et al., "Specific and Promiscuous Binding of Synthetic Copolymer 1 to Class II Major Histocompatibility Complex Molecules on Living Antigen Presenting Cells", Israeli Biochem. Soc., 1994, 21-22 (Abstract).

Fridkis-Hareli, et al., "Synthetic Copolymer 1 Inhibits the Binding of MBP, PLP and MOG Peptides to Class II Major Histocompatibility Complex Molecules on Antigen Presenting Cells" in Neurochem Mtg., Aug. 14-19, 1994, (Abstract).

Fridkis-Hareli, et al., "Synthetic Copolymer 1 Inhibits the Binding of MBP, PLP and MOG Peptides to Class II Major Histocompatibility Complex Molecules on Antigen-Presenting Cells", J. Neurochem., 1994, 63(Suppl. I), 561.

Fridkis-Hareli, et al., "Synthetic Copolymer I and Myelin Basic Protein Do Not Undergo Processing Prior to the Binding to Class II Major Histocompatibility Complex Molecules on Antigen Presenting Cells", Israeli Immunol. Soc., May 3-4, 1994 (Abstract).

Fridkis-Hareli et al., "Synthetic Copolymer 1 and MBP do not require processing prior to the binding to class II MHC Molecules on Antigen Presenting cells"Dept. Chem. Immunol, Weizmann Inst. 1994.

Fridkis-Hareli, et al., "Synthetic Copolymer 1 and Myelin Basic Protein Do Not Require Processing Prior to Binding to Class II Major Histocompatibility Complex Molecules on Living Antigen-Presenting Cells", Cell. Immunol., 1995, 163, 229-236.

Fridkis-Hareli, et al., "Promiscuous Binding of Synthetic Copolymer 1 to Purified HLA-DR Molecules", J. Immunol., 1998, 160, 4386-4397.

Fridkis-Hareli, et al., "Synthetic Amino Acid Copolymers that Bind to HLA-DR Proteins and Inhibit Type II Collagen-reactive T Cell Clones", Proc. Natl. Acad. Sci. USA, Oct. 1998, 95, 12528-12531.

Fridkis-Hareli, et al., "Binding of Random Copolymers of Three Amino Acids to Class II MHC Molecules", Intl. Immunol., 1999, 11(5): 635-641.

Fridkis-Hareli, et al., "Synthetic Peptides that Inhibit Binding of the Collagen Type II 261-273 Epitope to Rheumatoid Arthritis-Associated HLA-DR1 and DR4 Molecules and Collagen-Specific T-cell Responses", Database HCAPLUS on STN, Department of Clinical Immunology, Aarhus University Hospital, Aarhus, Denmark, HCAPLUS AN: 2000:455053, Human Immunology, 2000, 61(7), 640-650 (Abstract).

Grgacic, et al., "Cell-mediated Immune Response to Copolymer 1 in Multiple Sclerosis Measured by the Macrophage Procoagulant Activity Assay", Int. Immunol., 1990, 2(8), 713-718.

Gurevich, "Study of the MHC-competition Between BP and Cop 1 Using Human Cytotoxic T-cell Clones", Israel J. Med. Sci., 1993 (Abstract).

Harrison and Hafler, "Antigen-Specific Therapy for Autoimmune Disease", Current Opin. Immunol., 2000, 12(6): 704-711.

Henry, Celia M., "Special Delivery", Chem. and Eng. News, Sep. 18, 2000, 49-65.

Herzenberg, et al., "Lack of Immune Response Gene Control for Induction of Epitope-specific Suppression by TGAL Antigen", Nature, 1982, 295: 329-331 (Abstract).

Itoh M., "Selective Protection of alpha or Side-chain Carboxyl Groups and Glutamic Acid. A Facile Synthesis of beta-Aspartyl and gamma-Glutamyl Peptides," 1969, 17(8), pp. 1679-1686.

Jacobs, et al., "Advances in Specific Therapy for Multiple Sclerosis", Curr. Opin. Neurol., 1994, 7, 250-254.

Johnson, "Clinical Studies in Copolymer 1 Therapy for Exacerbating-remitting Multiple Sclerosis", in Congress for "Advances in the Understanding and Treatment of Multiple Sclerosis", Boston (USA), Oct. 28-29, 1992.

Johnson, "Experimental Therapy of Relapsing-Remitting Multiple Sclerosis with Copolymer-1", Ann. Neurol., 1994, 36(Suppl.), S115-S117.

Johnson, K.P., (1995) Neurology, vol. 45, pp. 1268-1276 (Abstract only).

Johnson, Management of Relapsing/Remitting Multiple Sclerosis with Copolymer 1 (Copaxone), Chemical Abstracts, 1996, vol. 125, p. 291993b.

Johnson, K.R. et al., Management of Relapsing/Remitting Multiple Sclerosis with Copolymer 1 (Copaxone), Multiple Sclerosis, 1996, vol. 1, No. 16, pp. 325-326, (Abstract).

Ju, et al., "Idiotypic Analysis of Antibodies Against the Terpolymer L-glutamic Acid 60-L-alanine30-L-tyrosine10 (GAT). IV. Induction of CGAT Idiotype Following Immunization with Various Synthetic Polymers Containing Glutamic Acid and Tyrosine", Eur. J. Immunol., 1979, 9(7): 553-560 (Abstract).

Kay, et al., "The Mechanism of Action of FK 506", Transplantation Proceedings, 1990, 22(1, Suppl. 1), 96-99.

Keith, et al., "The Effect of COP 1, a Synthetic Polypeptide, on Chronic Relapsing Experimental Allergic Encephalomyelitis in Guinea Pigs" J. Neurol. Sci., 1979, 42, 267-274.

Keleman, et al., "Graft-versus-Host Disease in Bone Marrow Transplantation: Experimental, Laboratory, and Clinical Contributions of the Last Few Years", Int. Arch. Allergy Immunol., 1993, 102, 309-320.

Kepsutlu, et al., "Evaluation of Chitosan Used as an Excipient in Tablet Formulations", Database HCAPLUS on STN, Department of Pharmaceutical Technology, Gulhane Military Medical Academy, Ankara, 06018, Turkey, HCAPLUS AN: 1999: 590411, Acta. Pol. Pharm. 1999, 56(3), 227-235 (Abstract).

Korczyn, et al., "Safety profile of copolymer 1: analysis of cumulative experience in the United States and Israel", J. Neurol, 1996, vol. 243 (Suppl. 1): S23-S26.

Kobayashi et al., "HLA-DR, DQ and T cell antigen receptor constant beta genes in Japanese patients with ulcerative colitis", Clinical Experimental Immunology, Jun. 1990, 80(3): 400-3.

Kott, et al., "COP-1 Increases Suppressor Cells Number in Multiple Sclerosis", Israel Neurological Assoc., Dec. 19-20, 1994, Herzliya (Israel), 17.

Kropshofer, et al., "Self-Peptides from Four HLA-DR Alleles Share Hydrophobic Anchor Residues Near the NH2-Terminal Including Proline as a Stop Signal for Trimming", J. Immunol., 1993, 151:(9) 4732-4742.

Lai et al., "Complementation of Class II a Alleles in the Immune Response to (Glulystyr) Polymers", Exp. Clin. Immunogenet., 1986, 3(1): 38-48 (Abstract).

Lai et al., "Monoclonal T Cell Responses to Two Epitopes on a Single Immunogen Controlled by Two Distinct Genes", *J. Immunol.*, 1986, 136(10): 3799-3804 (Abstract).

Lando et al., (1979) "Effect of Cyclophosphamide on Suppressor Cell Activity in Mice Unresponsive to EAE", J. Immunol., vol. 123, No. 5, pp. 2156-2160.

Lando, et al., "Experimental Allergic Encephalomyelitis in Mice—Suppression and Prevention with COP-1", *Israel J. Med. Sci.*, 1979, 15, 868-869 (Abstract).

Lee, et al., "Oral Route of Peptide and Protein Drug Delivery" in *Advances in Parenteral Sciences* (Vincent H.L. Lee, ed., Marcel Dekker, Inc., 1990) 691-738.

Li et al., "Glatiramer Acetate Blocks the Activation of THP-1 Cells by Interferon-γ", *Eur. J. Pharmacol.*, 1998, 342: 303-310.

Lisak, et al., "Effect of Treatment with Copolymer 1 (Cop-1) on the in Vivo and in Vitro Manifestations of Experimental Allergic Encephalomyelitis (EAE)", *J. Neurol. Sci.*, 1983, 62, 281-293.

Lombardi et al., "Common Human Leukocyte Antigen Alleles in Pemphigus Vulgaris and Pemphigus Foliaceus Italian Patients", *J. Invest. Dermatol.*, Jul. 1999 113(1):107-110.

Lovell, K. and Jones, M., "CNS Infections, Spongiform Encephalopathy and Demyelinating Diseases," Karol Marcinkowski U. Med. Sci., Dept. Pathol., Poland, last updated on Apr. 20, 2003, URL:http://ampat.amu.edu.pl/guzyuno/CNS_INFE.HTM.

Lymberi et al., *Arch. Hellen Med.*, 16(4), Jul.-Aug. 1999, 337-351.

Matsunaga et al., "Complementation of Class II A Alleles in the Immune Response to (Glu-Lys-Tyr) Polymers", *Yokohama Med. Bull.*, 1988, 39(1-2): 9-19 (Abstract).

Maurer et al., "Interpretations of Immune Responses of Mice to Poly(Glu6OLys40), its Modified Derivatives, and the Terpolymers Poly (Glu55Lys37Leu8) and Poly (Glu56Lys37Ser7)", *Clin. Immunol. Immunopathol.*, 1980, 15(3): 344-356 (Abstract).

McDermott, et al., "Antigen-induced Suppression of Experimental Allergic Neuritis in the Guinea Pig", *J. Neurol. Sci.*, 1980, 46, 137-143.

McGavern, et al., "Do Antibodies Stimulate Myelin Repair in Multiple Sclerosis", *The Neuroscientist*, 1999, 5(1): 19-28.

Meiner, "COP-1 Multicenter Clinical Trial in Exacerbating-remitting Multiple-Sclerosis: One Year Follow-up", *J. Neurol.*, 1991(Suppl. 1) (Abstract).

Meiner, et al., "The Israeli COP-1 Multicenter Clinical Trial in Exacerbating-remitting Multiple Sclerosis—Two-year Follow-up", in *9th Congress of the European Committee for Treatment and Research in Multiple Sclerosis*, Florence (Italy), Oct.-Nov. 1993, 48 (Abstract).

Mengle-Gaw, "The Major Histocompatibility Complex (MHC)", in *Encycl. Molecular Bio.* (Oxford Blackwell Science Ltd, 1994) 602-606.

Milo, et al., "Inhibition of Myelin Basic Protein-specific Human T-cell Lines by COP-1", *Israel J. Med. Sci.*, 1992, 28, 486 (Abstract).

Milo, et al., "Copolymer-1 (COP-1) Regulates Class II MHC Expression and Cytokine Synthesis in the THP-1 Monocyte-Macrophage Cell Line", *The IBC Conference on Multiple Sclerosis*, San Diego (USA), Dec. 10, 1993 (Abstract).

Milo, et al., "Additive Effects of COP-1 and IFN-Beta on Immune Responses to Myelin Basic Protein", *Neurol.*, 1994, 44(Suppl. 2), A212.

Milo et al., Assaf Harofeh Med. Ctr., Tel-Aviv U. of Maryland Sch. Med., 1994, 22.

Milo, et al., "Additive Effects of Copolymer-1 and Interferon β-1b on the Immune Response to Myelin Basic Protein", *J. Neuro.*, 1995, (61), 185-193.

Milo, et al., "Copolymer-1 and Interferon-β Additively Suppress the Immune Response to Myelin Basic Protein by Inhibiting Antigen Presentation", *J. Neuroimmunol.*, 1994, 54, 183 (Abstract).

Milo, et al., "Additive Effects of Copolymer-1 and Interferon β on the Immune Response to Myelin Basic Protein", *J. Neuroimmunol.*, 1995, 61, 185-193.

Myers, et al., "The Peculiar Difficulties of Therapeutic Trials for Multiple Sclerosis", *Neurologic Clinics*, 1990, 8(1), 119-141.

Nightingale, et al., "Access to Investigational Drugs for Treatment Purposes", *Am. Family Physician*, 1994, 50(4), 845-847.

O'Connor, et al., "Powders" in *The Science and Practice of Pharmacy*, Remington, 1995, 2, 1598-1614.

Pavelko, et al., "Acceleration in the Rate of CNS Remyelination in Lysolecithin-Induced Demyelination", *J. Neurosci.*, 1998, 18(7): 2498-2505.

Pender, et al. "Prevention of autoimmune attack and disease progression in Multiple Sclerosis: Current therapies and future prospects", *Int. Med. Journal*, 2002, 32: 554-563.

Porter, "Coating of Pharmaceutical Dosage Forms," *The Science and Practice of Pharmacy*, Remington, 1995, 2, 1650-1659.

Prat, et al., "Lymphocyte Migration and Multiple Sclerosis: Relation with Disease Course and Therapy," *Ann. Neurol.*, 1999, 46: 253-256.

Puri, et al., "Modulation of the Immune Response in Multiple Sclerosis", *J. Immunol.*, 1997, 158, 2471-2476.

Racadot, E. et al., "Treatment of Multiple Sclerosis with Anti-CD4 Monoclonal Antibody", *J. of Autoimmunity*, 1993, vol. 6, pp. 771-786.

Racke, et al., "Copolymer-1-induced Inhibition of Antigen-specific T Cell Activation: Interference with Antigen Presentation", *J. Neuroimmunol.*, 1992, 37, 75-84.

Reilly, Jr., W.J., "Pharmaceutical Necessities", *The Science and Practice of Pharmacy*, Remington, 1995, 2, 1380-1416.

Rodriguez, *Neurological Therapeutics*, 1998, 15(3): 245-250.

Rolak, "Copolymer-I Therapy for Multiple Sclerosis", *Clin. Neuropharmacology*, 1987, 10(5), 389-396.

Rothbard, et al., "Interactions Between Immunogenic Peptides and MHC Proteins", *Annu. Rev. Immunol.*, 1991, 9, 527-565.

Salvetti, et al., "Myelin Basic Protein T Cell Epitopes in Patients with Multiple Sclerosis", *Department of Neurological Sciences*, University of Rome, La Sapienza 1991, 72 (Abstract).

Sela, et al., *Vaccine*, 1992, vol. 10, No. 14, pp. 991-999.

Schlegel, et al., "Prevention of Graft-Versus-Host Disease by Peptides Binding to Class II Major Histocompatibility Complex Molecules", *Blood*, 1994, 84(8), 2802-2810.

Schlegel, et al., "Inhibition of Allorecognition and Prevention of Graft-vs-host Disease (GVHD) by GLAT, a Synthetic Polymer with Promiscuous Binding to Murine and Human MHC Class II Molecules", in *Am. Soc. Hematology, 37th Annual Meeting*, Seattle, WA (USA), Dec. 1-5, 1995, 224a,883 (Abstract).

Schwartz, et al., "Gene Complementation in the T Lymphocyte Proliferative Response to Poly(Glu57Lys38Tyr5): Evidence for Effects of Polymer Handling and Gene Dosage", *J. Immunol.*, 1979, 123(1): 272-278 (Abstract).

Sela, et al., "Experimental Allergic Encephalomyelitis" in *Menarini Series on Immunopathology, vol. 1, First Symposium of Organ Specific Autoimmunity*, Cremona, Italy, Jun. 1977, (Miescher P.A. ed., Schwabe Co., Basel, 1978), 9-21.

Sela, et al., "Suppressive Activity of COP-1 in EAE and its Relevance to Multiple Sclerosis", *Bull. Inst. Pasteur*, 1990, 88, 303-314.

Sela, "Polymeric Drugs as Immunomodulatory Vaccines Against Multiple Sclerosis", *Makromol. Chem. Macromol. Symp.*, 1993, 70/71, 147-155.

Sridama et al., "HLA Immunogenetic Heterogeneity in Black American Patients with Graves' Disease", *Arch. Intern. Med.*, 1987, 147:229-231.

Stark, "Expanded Clinical Trials of Treatments for Multiple Sclerosis (MS): Copolymer 1 (COP-1) Treatment Investigational New Drug (IND) Program", *Ann. Neurol.*, 1994, 36, 114-115.

Starzl, "Introduction", *Transplantation Proceedings*, 1990, 22 ( 1, Suppl. 1), 5.

Sykes, "Immunobiology of Transplantation", *Faseb J.*, 1996, 10, 721-730.

Tarcic, et al., "Copolymer 1 (Copaxone) from an Idea to a Drug for Treatment of Multiple Sclerosis" Database HCAPLUS on STN, Israel: AN 1997:333270. Kim, Handasa Kim, 1997, 28 (14), 16-18 (Abstract).

Teitelbaum, et al., "Suppression of Experimental Allergic Encephalomyelitis by a Synthetic Polypeptide", *Eur. J. Immunol.*, 1971, 1, 242-248.

Teitelbaum, et al., "Suppression of Experimental Allergic Encephalomyelitis by a Synthetic Polypeptide", *Israel J. Med. Sci.*, 1971, 7, 630-631 (Abstract).

Teitelbaum, et al., "Protection Against Experimental Allergic Encephalomyelitis", *Nature*, 1972, 240, 564-566.

Teitelbaum, et al., "Suppression by Several Synthetic Polypeptides of Experimental Allergic Encephalomyelitis Induced in Guinea Pigs and Rabbits with Bovine and Human Basic Encephalitogen", *Eur. J. Immunol.*, 1973, 3, 273-279.

Teitelbaum, et al., "Dose-response Studies on Experimental Allergic Encephalomyelitis Suppression by COP-1", *Israel J. Med. Sci.*, 1974, 10(9), 1172-1173.

Teitelbaum, et al., "Suppression of Experimental Allergic Encephalomyelitis in Rhesus Monkeys by a Synthetic Basic Copolymer", *Clin. Immunol. Immunopath.*, 1974, 3, 256-262.

Teitelbaum, et al., "Suppression of Experimental Allergic Encephalomyelitis in Baboons by Cop 1", *Israel J. Med. Sci.*, 1977, 13, 1038 (Abstract).

Teitelbaum, et al., "Blocking of Sensitization to Encephalitogenic Basic Protein in Vitro by Synthetic Basic Copolymer (COP 1)", *Cell Biology and Immunology of Leukocyte Function* (Academic Press, New York, 1979) 681-685.

Teitelbaum, "Suppression of Experimental Allergic Encephalomyelitis with a Synthetic Copolymer—Relevance to Multiple Sclerosis", *Humoral Immunity in Neurological Diseases* (Karcher D., Lowenthal A. & Strosberg A.D., eds., Plenum Publishing Corp., 1979) 609-613.

Teitelbaum, et al., "Monoclonal Antibodies to Myelin Basic Protein Cross React with Synthetic EAE-suppressive Copolymer, COP 1", *Proc. 7th Eur. Immunol. Mtg.*, Jerusalem, Sep. 8-13, 1985 (Abstract).

Teitelbaum, et al., "Specific Inhibition of the T-cell Response to Myelin Basic Protein by the Synthetic Copolymer Cop 1", *Proc. Natl. Acad. Sci. USA*, 1988, 85, 9724-9728.

Teitelbaum, et al., "Clinical Trial of Copolymer 1 in Multiple Sclerosis" *J. Israel Med. Assoc.*, 1989, CXVI(9), 453-456.

Teitelbaum, et al., "Cross-reactions and Specificities of Monoclonal Antibodies Against Myelin Basic Protein and Against the Synthetic Copolymer 1", *Proc. Natl. Acad. Sci.* (USA), 1991, 88, 9528-9532.

Teitelbaum, et al., "Immunological Parameters in a Multicenter Clinical Trial of COP1 in Multiple Sclerosis (MS): A 2-year Follow-up", *Neurol.*, 1994, 44(Suppl. 2), A358.

Teitelbaum, et al., "Copolymer 1 Inhibits Chronic Relapsing Experimental Allergic Encephalomyelitis Induced by Proteolipid Protein (PLP) Peptides in Mice and Interferes with PLP-specific T Cell Responses", *J. Neuroimmunol.*, 1996, 64, 209-217.

Teitelbaum, et al., "Copolymer 1 from the Laboratory to FDA", *Israel J. Med. Sci.*, 1997, 33, 280-284.

Teitelbaum D., "Copolymer 1 induces T cells of the T helper type 2 that crossreact with myelin basic protein and suppress experimental auto immune encephalomyelitis," *Proc. Natl. Acad. Sci. U.S.A.*, Sep. 1997, 94(20), 10821-10826.

t'Hart, et al., "The Use of Animal Models to Investigate the Pathogenesis of Neuroinflammatory Disorders of the Central Nervous System", *Curr. Opin. Neurol.*, 2003, vol. 16, 375-383.

Teva, et al., "Copolymer-1 Glatiramer Acetate Copaxone Agent for Multiple Sclerosis", *Drugs of the Future*, 1998, vol. 23, No. 2, pp. 213-214.

The COP-1 Multicenter Clinical and Research Group Study, "COP-1 Multicenter Trial in Relapsing Remitting Multiple Sclerosis: 3 Year Follow Up", *Abstracts of Symposia and Free Communications*, Barcelona (Spain), Jun. 25-29, 1994, 241 (Suppl. 1), 6.

Thompson, "MCQ Tutor: Medical Immunology Multiple Choice Questions", *Immunol. Today*, 1985, 6(4), 141.

Tisch, et al., "Antigen-specific immunotherapy: Is it a Real Possibility to Combat T-Cell-Mediated autoimmunity?" *Proc. Natl. Acad. Sci. U.S.A.*, 1994, 91, 437-438.

Trannoy, et al., "Epitope-specific Regulation of the T Cell Repertoire: Carrier Recognition in Association with I-E or I-A Does Not Influence the Restriction of Hapten-Specific T Cells", *Eur. J. Immunol.*, 1985, 15(12): 1215-1221 (Abstract).

Ure, D.R. et al., "Polyreactive Antibodies to Glatiramer Acetate Promote Myelin Repair in Murine Model of Deymelinating Disease", *FASEB Journal*, 2002, vol. 16, pp. 1260-1262.

Vandenbark, A.A. et al., "Specificity of T Lymphocyte Lines for Peptides of Myelin Basic Protein", *The J. of Immunology*, 1985, vol. 135, pp. 229-233.

Van den Bogaerde, et al., "Induction of Long-Term Survival of Hamster Heart Xenografts in Rats", *Transplantation*, 1991, 52, 15-20.

Van Noort, et al., "Cell Biology of Autoimmune Diseases", *International Review of Cytology*, 1998, 178: 127-205.

Wan et al., "HLA-DR and HLA-DQ Polymorphism in Human Thyroglobulin-Induced Autoimmune Thyroiditis: DR3 and DQ8 Transgenic Mice are Susceptible", *Human Immunology*, Apr. 2002, 63(4):301-10.

Warrington, et al., "Human Monoclonal Antibodies Reactive to Oligodendrocytes Promote Remyelination in a Model of Multiple Sclerosis", *Neurobiology*, 2000, 97(12): 6820-6825.

Warrington, et al., "Immunoglobulin-Mediated CNS Repair", *J. Allergy Clin. Immunol.*, 2001, S121-S125.

Webb, et al., "Further Studies on the Suppression of Experimental Allergic Encephalomyelitis by Synthetic Copolymer", *Israel J. Med. Sci.*, 1972, 8, 656-657 (Abstract).

Webb, et al., "In Vivo and in Vitro Immunological Cross-reactions between Basic Encephalitogen and Synthetic Basic Polypeptides Capable of Suppressing Experimental Allergic Encephalomyelitis", *Eur. J. Immunol.*, 1973, 3, 279-286.

Webb, et al., "Suppression of Experimental Allergic Encephalomyelitis in Rhesus Monkeys by a Synthetic Basic Copolymer", *Isr. J. Med. Sci.*, 1975, 11, 1388 (Abstract).

Webb, et al., "Molecular Requirements Involved in Suppression of EAE by Synthetic Basic Copolymers of Amino Acids", *Immunochem.*, 1976, 13, 333-337.

Webster's II New Riverside University Dictionary, The Riverside Publishing Company, 1984, 933.

Weilbach, F.X. et al., "Disease Modifying Treatments for Muliple Sclerois", *CNS Drugs*, 1999, vol. 11(2), pp. 133-167.

Weinshenker, et al., "Natural History and Treatment of Multiple Sclerosis", *Current Opinion in Neurol. and Neurosurgery*, 1992, 5, 203-211.

Wiesemann, et al., (2001) "Glatiramer Acetate Induces IL-13/Il-5 Secretion in Native T Cells", Journal of Neuroimmunology, vol. 119, No. 1, pp. 137-144.

Wender, "Copolymer 1 (COP-1) in the Treatment of Multiple Sclerosis (letter)", *Pol. Neuro. Neurosurg. Pol.*, 1990, 24, 113.

Winer, "COP 1 Therapy for Multiple Sclerosis", *New Eng. J. Med.*, 1987, 317(7), 442-444.

Zhang, J.W. et al., "Murine Monoclonal Anti-Myelin Basic Protein (MBP) Antibodies Inhibit Proliferationa dn Cytotoxicity of MBP-Specific Human T Cell Clones", *J. of Neuroimmunology*, 1989, vol. 24, pp. 87-94.

Zisman, et al., "Direct Binding of a Synthetic Multichain Polypeptide to Class II Major Histocompatibility Complex Molecules on Antigen-presenting Cells and Stimulation of a Specific T-cell Line Require Processing of the Polypeptide", *Proc. Natl. Acad. Sci. USA*, 1991, 88(21): 9738-9742 (Abstract).

Zisman, et al., "Dichotomy Between the T and the B Cell Epitopes of the Synthetic Polypeptide (T,G)-A—L", *Eur. J. Immunol.*, 1994, 24(10): 2497-2505 (Abstract).

"Copaxone" in *Physician's Desk Reference*, 2000, Medical Economics Co., Inc., Montvale, NJ, 3115.

Pharmacia Biotech Directory, 1996, pp. 340-341.

"About Copaxone", Internet Article, URL:http//www.mswatch.com/therapy/section.aspx?SectionId=789eabf5-3a07-4dff-a7ee-0d4ad1381a6d.

Copaxone® (glatiramer acetate injection), prescribing information, http://www.copaxone.com/pdf/PrescribingInformation.pdf.

PCT International Search Report issued Sep. 18, 2003 for International Application Publication WO/2003/048735.

PCT International Preliminary Report on Patentability issued Aug. 27, 2004 for International Application WO/2003/048735.

U.S. Appl. No. 09/359,099, filed Jul. 12, 1999, Strominger, et al.
U.S. Appl. No. 10/577,588, filed Apr. 27, 2006, Schmidt et al.
U.S. Appl. No. 12/074,106, filed Feb. 22, 2008, Pinchasi, et al.
U.S. Appl. No. 12/231,292, filed Aug. 29, 2008, Aharoni et al.
U.S. Appl. No. 12/315,009, filed Nov. 26, 2008, Stark et al.

Pennesi, et al., "A Humanized Model of Experimental Autoimmune Uveitis in HLA Class II Transgenic Mice", The Journal of Clinical Investigation, Apr. 2003, vol. 111, No. 8, 1171-1180.

Rodriguez, M. et al., "Immunoglobulins Reactive with Myelin Basic Protein Promote CNS Remyelination", Neurology, 1996, vol. 46, pp. 538-545.

Teitelbaum, (1992) "Synthetic Copolymer 1 Inhibits Human T-cell Lines Specific for Myelin Basic Protein", Proc. Natl. Acad. Sci. USA, vol. 89, pp. 137-141.

Merck Manual of Diagnosis and Therapy, *Merck Research Laboratories*, Whitehouse Section, N.J., 17th Ed., 1999, pp. 1300-1303, pp. 1312-1317.

Jul. 21, 2006 Office Action in connection with U.S. Appl. No. 10/313,726.
Mar. 28, 2007 Final Office Action in connection with U.S. Appl. No. 10/313,726.
Jun. 27, 2007 Advisory Action in connection with U.S. Appl. No. 10/313,726.
Oct. 5, 2007 Office Action in connection with U.S. Appl. No. 10/313,726.
Jun. 6, 2008 Notice of Allowance and Allowability including Notice of Fees in connection with U.S. Appl. No 10/313,726.
Dec. 9, 2005 Official Action in connection with Chinese Application No. 02827773.2.
Jun. 16, 2006 Official Action in connection with Chinese Application No. 02827773.
Dec. 1, 2006 Notice of Allowance in connection with Chinese Application No. 02827773.2.
Jul. 27, 2004 Communication Pursuant to Rules 109 and 110 E.P.C. in connection with European Application No. 02790028.1.
Jul. 30, 2008 Communication Pursuant to Article 153(7) E.P.C. in connection with European Application No. 02790028.
Dec. 25, 2007 Official Action in connection with Japanese Application No. 2003-549881.
Mar. 24, 2009 Official Action in connection with Japanese Application No. 2003-549881.
Oct. 28, 2004 Official Action in connection with New Zealand Appliccation No. 533327.
Feb. 20, 2006 Official Action in connection with New Zealand Application No. 533327.
Nov. 2, 2006 Notice of Acceptance in connection with New Zealand Application No. 53332.
May 22, 2006 Notice to Submit Response in connection with Korean Application No. 10-2004-7008518.
Sep. 15, 2006 Notice of Allowance in connection with Korean Application No. 10-2004-7008518.

U.S. Appl. No. 12/586,459, filed Sep. 22, 2009, Gad et al.
U.S. Appl. No. 12/660,581, filed Mar. 1, 2010, Kreitman et al.
U.S. Appl. No. 10/543,764, filed Jul. 18, 2005, Aharoni et al.
U.S. Appl. No. 12/660,258, filed Feb. 22, 2010, Lancet et al.
U.S. Appl. No. 12/861,655, filed Aug. 23, 2010, Stark et al.
U.S. Appl. No. 12/761,367, filed Apr. 15, 2010, Altman et al.
U.S. Appl. No. 12/785,125, filed May 21, 2010, Altman et al.

Nov. 26, 2009 Amendment after Allowance in connection with Canadian Patent Application No. 2,469,393.
Notice of Allowance in connection with Canadian Patent Application No. 2,469,393.
Jul. 14, 2009 Voluntary Amendment in connection with Canadian Patent Application No. 2,469,393.
Nov. 7, 2008 Response to Official Action in connection with Canadian Patent Application No. 2,469,393.
Aug. 27, 2008 Official Action in connection with Canadian Patent Application No. 2,469,393.
Apr. 17, 2008 Response to Official Action in connection with Canadian Patent Application No. 2,469,393.
Oct. 17, 2007 Official Action in connection with Canadian Patent Application No. 2,469,393.
Amendment in Response to Dec. 9, 2005 Official Action submitted in connection with Chinese Application No. 02827773.2.
Amendment in Response to Jun. 16, 2006 Official Action in connection with Chinese Application No. 02827773.2.
Jul. 7, 2009 Communication Pursuant to Article 94(3) E.P.C. in connection with European Application No. 02190028.1.
Nov. 10, 2009 Response to Official Action Pursuant to Article 94(3) EPC in connection with European Application No. 02790028.1.
Apr. 8, 2009 Official Action in connection with Indian Application No. 1752/DELNP/2004.
Jan. 2, 2009 Response to Apr. 8, 2008 Official Action submitted in connection with Indian Application No. 1752/DELNP/2004.
Mar. 16, 2009 Official Action in connection with Indian Application No. 1752/DELNP/2004.
Mar. 24, 2009 Response to Mar. 16, 2009 Official Action in connection with Indian Application No. 1752/DELNP/2004.
Amendment in Response to Dec. 28, 2007 Official Action in connection with Japanese Application No. 2003-549881.
Amendment in Response to Mar. 24, 2009 Official Action in connection with Japanese Application No. 2003-549881.
Jan. 26, 2006 Amendment in Response to Oct. 28, 2004 Official Action submitted in connection with New Zealand Application No. 533327.
Apr. 21, 2006 Amendment in Response to Feb. 20, 2006 Official Action in connection with New Zealand Application No. 533327.
Amendment in Response to May 22, 2006 Official Action in connection with Korean Application No. 10-2004-7008518.
Amendment in Response to Jun. 24, 2009 Official Action in connection with Mexican Application No. PA/a/2004/005433.
Sela et al., "Synthetic Approaches to Vaccines for infectious and autoimmune diseases" Vaccine, 1992, 10 (14), 991-999.

* cited by examiner

US 7,923,215 B2

PROCESS FOR THE MEASUREMENT OF THE POTENCY OF GLATIRAMER ACETATE

The present application is a continuation of U.S. Ser. No. 10/313,726, filed Dec. 4, 2002, now U.S. Pat. No. 7,429,374 which claims the benefit of U.S. Provisional Application No. 60/338,767, filed Dec. 4, 2001, the contents of which are hereby incorporated by reference.

Throughout this application, various references are cited, using shortened citations within parentheses. Full citations for these references can be found at the end of the specification, immediately preceding the claims. These publications, in their entireties, are hereby incorporated by reference into the application to more fully describe the state of the art to which the invention pertains.

FIELD OF THE INVENTION

The present invention relates to methods of standardizing the measurement of the potency of glatiramer acetate based on specific recognition of the glatiramer acetate by T cells.

BACKGROUND

It is desirable to standarize the measurement of the potency of pharmaceutical compositions as there is an optimum potency and quality of active component that is effective in treating the disease for which it is administered.

Glatiramer acetate (GA, also known as Copolymer-1 (Physician's Desk Reference), Copolymer 1, Cop-1 or COPAXONE®), is an approved drug for the treatment of multiple sclerosis (MS). Glatiramer acetate consists of the acetate salts of synthetic polypeptides, containing four naturally occurring amino acids (Physician's Desk Reference): L-glutamic acid, L-alanine, L-tyrosine, and L-lysine (Physician's Desk Reference) with an average molar fraction of L-glutamic acid: 0.129-0.153; L-alanine: 0.392-0.462; L-tyrosine: 0.086-0.100; L-lysine: 0.300-0.374, respectively. The average molecular weight of glatiramer acetate is 4,700-11,000 daltons (Physician's Desk Reference). Chemically, glatiramer acetate is designated L-glutamic acid polymer with L-alanine, L-lysine and L-tyrosine, acetate (salt) (Physician's Desk Reference). Its structural formula is:

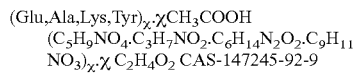

(Physician's Desk Reference). Glatiramer acetate is also written as: poly[L-Glu$^{13\text{-}15}$, L-Ala$^{39\text{-}46}$, L-Tyr$^{8.6\text{-}10}$, L-Lys$^{30\text{-}37}$].nCH$_3$COOH.

Glatiramer acetate was shown to suppress experimental autoimmune encephalomyelitis (EAE)—an experimental model for multiple sclerosis (MS) in various animal species (Lando et al., 1979; Aharoni, 1993). Studies of murine EAE suggested that the protection against EAE is mediated by T cell activity (Aharoni, 1993). This protection from active induction of EAE by mouse spinal cord homogenate, in which several auto-antigens are involved, could be adoptively transferred to normal recipients by injection of glatiramer acetate-specific T suppressor cells (Aharoni, 1993). In phase III clinical trials, daily subcutaneous injections of glatiramer acetate were found to slow progression of disability and reduce the relapse rate in exacerbating-remitting multiple sclerosis (Johnson, 1987). Processes of manufacturing glatiramer acetate are described in U.S. Pat. Nos. 3,849,550 and 5,800,808 and PCT International Publication No. WO 00/05250.

It is commonly accepted that a high level of antigen specificity is a feature of T cell activation. The T cells of the immune system recognize immunogenic peptides complexed to the major histocompatibility complex (MHC) class II or I molecules, expressed on antigen presenting cells (APCs). The specificity of antigen recognition by T cells is defined by several parameters: 1) affinity of the T cell receptor to the MHC peptide complex; 2) primary sequence of the antigenic peptide; and 3) synergistic effects of certain amino acid combinations within the antigenic peptide. Based on current knowledge on the mechanism of action of glatiramer acetate, it is believed that the biological activity of glatiramer acetate in MS is mediated by immunomodulation of T cell activity.

SUMMARY OF THE INVENTION

The subject invention provides a process for measuring the potency of a test batch of glatiramer acetate relative to the known potency of a reference batch of glatiramer acetate which comprises a. immunizing female (SJLXBALB/C)F1 mice between 8 and 12 weeks of age with a predetermined amount of glatiramer acetate from the reference batch;

b. preparing a primary culture of lymph node cells from the mice of step (a) 9-11 days after immunization;

c. separately incubating at least five reference samples, each of which contains a predetermined number of cells from the primary culture of step (b) and a predetermined amount of glatiramer acetate between 1 µg/ml and 25 µg/ml from a reference batch;

d. incubating at least two samples, each of which contains a predetermined number of cells from the primary culture of step (b) and a predetermined amount of glatiramer acetate from the test batch;

e. determining for each sample in steps (c) and (d), the amount of interleukin-2 secreted by the cells in each sample after 18-21 hours of incubation of such sample;

f. correlating the amounts of interleukin-2 secreted by the samples incubated with the test batch of glatiramer acetate with the amounts of interleukin-2 secreted by the samples incubated with the reference batch of glatiramer acetate so as to determine the potency of the test batch of glatiramer acetate relative to the reference batch of glatiramer acetate, wherein in each sample in steps (c) and (d), the predetermined number of cells is substantially identical, and wherein for each sample containing a predetermined amount of glatiramer acetate from the test batch there is a corresponding reference sample containing a substantially identical predetermined amount of glatiramer acetate from the reference batch.

The subject invention also provides a process for measuring the potency of a test batch of glatiramer acetate relative to the known potency of a reference batch of glatiramer acetate which comprises a. immunizing a test mammal with a predetermined amount of glatiramer acetate from the reference batch;

b. preparing a primary culture of cells from the test mammal of step (a) at a predetermined time after immunization;

c. separately incubating at least two reference samples, each of which contains a predetermined number of cells from the primary culture of step (b) and a predetermined amount of glatiramer acetate from a reference batch;

d. incubating at least two samples, each of which contains a predetermined number of cells from the primary culture of step (b) and a predetermined amount of glatiramer acetate from the test batch;

e. determining for each sample in steps (c) and (d), the amount of a cytokine secreted by the cells in each sample after a predetermined time period of incubation of such sample;

f. correlating the amounts of the cytokine secreted by the samples incubated with the test batch of glatiramer acetate with the amounts of the cytokine secreted by the samples incubated with the reference batch of glatiramer acetate so as to determine the potency of the test batch of glatiramer acetate relative to the reference batch of glatiramer acetate, wherein in each sample in steps (c) and (d), the predetermined number of cells is substantially identical, and wherein for each immunization sample containing a predetermined amount of glatiramer acetate from the test batch there is a corresponding reference sample containing a substantially identical predetermined amount of glatiramer acetate from the reference batch.

DETAILED DESCRIPTION

Figure 1:
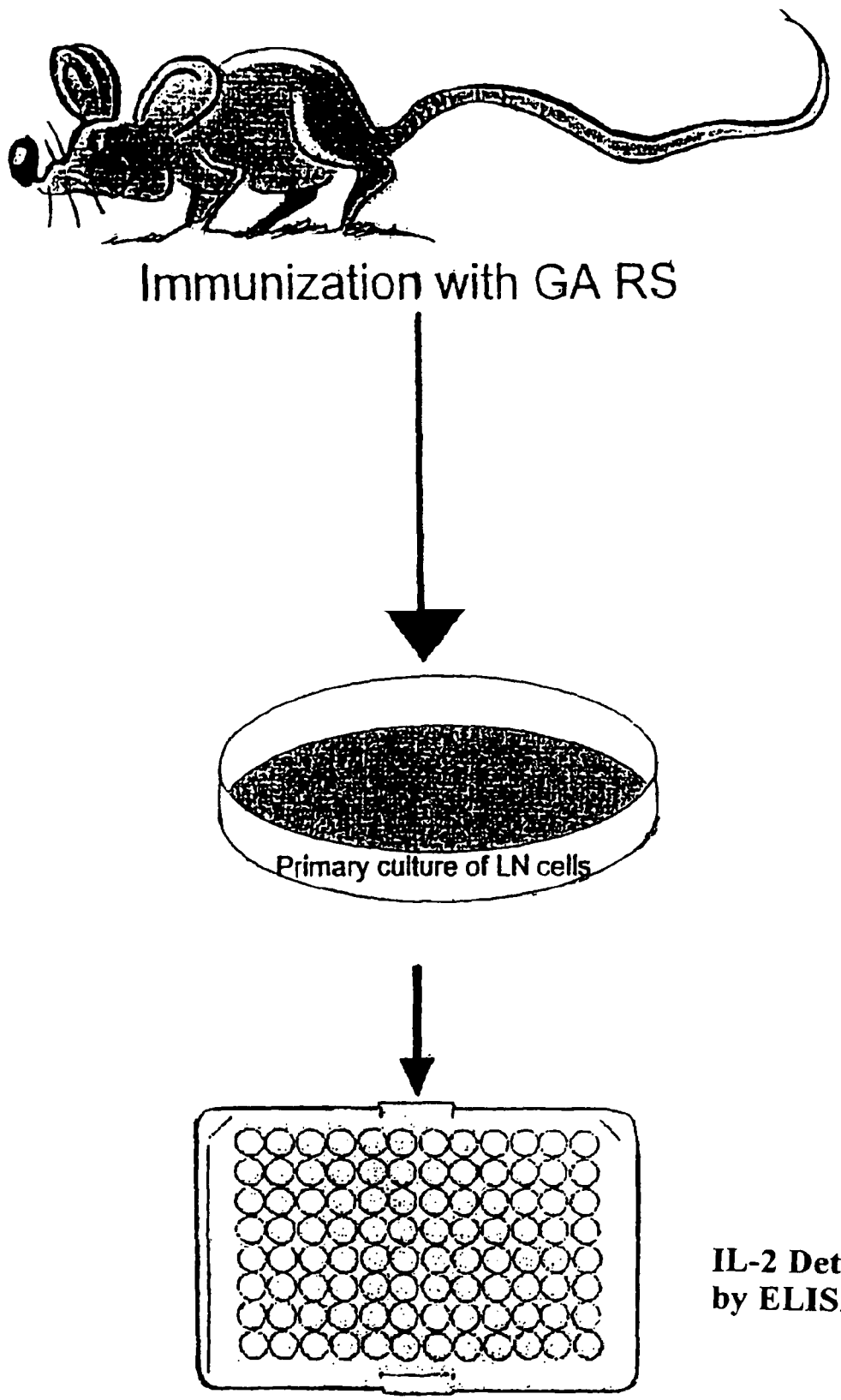
FIG. 1: Immunization with GA RS (Reference Standard). Primary culture of LN cells. IL-2 Detection by ELISA.

The subject invention provides a process for measuring the potency of a test batch of glatiramer acetate relative to the known potency of a reference batch of glatiramer acetate which comprises a. immunizing female (SJLXBALB/C)F1 mice between 8 and 12 weeks of age with a predetermined amount of glatiramer acetate from the reference batch.

b. preparing a primary culture of lymph node cells from the mice of step (a) 9-11 days after immunization;

c. separately incubating at least five reference samples, each of which contains a predetermined number of cells from the primary culture of step (b) and a predetermined amount of glatiramer acetate between 1 μg/ml and 25 μg/ml from a reference batch;

d. incubating at least two samples, each of which contains a predetermined number of cells from the primary culture of step (b) and a predetermined amount of glatiramer acetate from the test batch;

e. determining for each sample in steps (c) and (d), the amount of interleukin-2 secreted by the cells in each sample after 18-21 hours of incubation of such sample;

f. correlating the amounts of interleukin-2 secreted by the samples incubated with the test batch of glatiramer acetate with the amounts of interleukin-2 secreted by the samples incubated with the reference batch of glatiramer acetate so as to determine the potency of the test batch of glatiramer acetate relative to the reference batch of glatiramer acetate, wherein in each sample in steps (c) and (d), the predetermined number of cells is substantially identical, and wherein for each sample containing a predetermined amount of glatiramer acetate from the test batch there is a corresponding reference sample containing a substantially identical predetermined amount of glatiramer acetate from the reference batch.

In one embodiment, six reference samples are separately incubated in step (d).

The subject invention also provides a process for measuring the potency of a test batch of glatiramer acetate relative to the known potency of a reference batch of glatiramer acetate which comprises a. immunizing a test mammal with a predetermined amount of glatiramer acetate from the reference batch;

b. preparing a primary culture of cells from the test mammal of step (a) at a predetermined time after immunization;

c. separately incubating at least two reference samples, each of which contains a predetermined number of cells from the primary culture of step (b) and a predetermined amount of glatiramer acetate from a reference batch;

d. incubating at least two samples, each of which contains a predetermined number of cells from the primary culture of step (b) and a predetermined amount of glatiramer acetate from the test batch;

e. determining for each sample in steps (c) and (d), the amount of a cytokine secreted by the cells in each sample after a predetermined time period of incubation of such sample;

f. correlating the amounts of the cytokine secreted by the samples incubated with the test batch of glatiramer acetate with the amounts of the cytokine secreted by the samples incubated with the reference batch of glatiramer acetate so as to determine the potency of the test batch of glatiramer acetate relative to the reference batch of glatiramer acetate, wherein in each sample in steps (c) and (d), the predetermined number of cells is substantially identical, and wherein for each immunization sample containing a predetermined amount of glatiramer acetate from the test batch there is a corresponding reference sample containing a substantially identical predetermined amount of glatiramer acetate from the reference batch.

In one embodiment, the cytokine is an interleukin.
In a preferred embodiment, the interleukin is interleukin-2.
In another embodiment, the interleukin is interleukin-6.
In a further embodiment, the interleukin is interleukin-10.
In an added embodiment, the cytokine is interferon-gamma.
In one embodiment, the mammal produces T cells specific to glatiramer acetate reference standard.
In another embodiment, the mammal is a rodent.
In still another embodiment, the rodent is a mouse.
In an additional embodiment, the mouse is a female (SJLX-BALB/C)F1 mouse.

In a further embodiment, the mammal is about 8 to about 12 weeks old.
In yet another embodiment, the cells are lymph node cells.
In one embodiment, the cells are spleen cells.

The subject invention further provides a process for preparing a batch of glatiramer acetate as acceptable for pharmaceutical use which comprises a. preparing a batch of glatiramer acetate;
b. measuring the relative potency of the batch according to the process indicated hereinabove; and
c. qualifying the batch as acceptable for pharmaceutical use if the relative potency so measured is between 80% and 125% of the reference batch of glatiramer acetate.

Additionally, the subject invention provides a process for preparing glatiramer acetate acceptable for pharmaceutical use which comprises a. preparing a batch of glatiramer acetate;
b. measuring the relative potency of the batch according to the process indicated hereinabove; and
c. qualifying the batch as acceptable for pharmaceutical use if the relative potency so measured is between 80% and 125% of the reference batch of glatiramer acetate.

Thus, the present invention provides the standardization of the measurement of the potency of GA. The potency test quantitatively determines the biological activity of GA. This is the first showing ever of such a test. This standardization method is essential in order to show batch to batch reproducibility with regards to potency and quality of DS and DP. In the context of this application, DS refers to the active ingredient, i.e., GA. DP is used to indicate the finished product, i.e., Copaxone®. RS denotes a batch of glatiramer acetate having an average molecular weight of about 7000 Da.

The subject invention makes use of the observation that T cells incubated with a cytokine, e.g., IL-2, proliferate in response to that cytokine (Lisak et al., 1974).

The examples which follow describe the invention in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

EXPERIMENTAL EXAMPLES

General Procedure Outline

Mice were immunized with 250 µg GA RS in CFA. GA RS was produced as described in U.S. Pat. No. 5,800,808 or PCT International Publication No. WO 00/05250. The GA RS was chosen based on the chemical and biological properties being in the midrange of Copaxone® as described above. After 9-11 days, a primary culture of LN cells was prepared, and the cells were incubated with various concentrations of GA RS and with test samples. Following 18-21 hours of incubation at 37° C. in a humidified $CO_2$ incubator, the culture media were collected and the level of IL-2 was measured by ELISA. The T-cell response to each DS batch were tested at two concentrations (within the linear range), and the % potency of the DS batch was calculated relative to that of the GA RS batch.

Example 1

Standard Procedure

Purpose

The purpose of this procedure was to determine the relative potency of GA DS batch in vitro, using GA RS-specific T cells.

Equipment

Laminar hood, hemacytometer, disposable cover slips, cell counter centrifuge, temperature-controlled shaking incubator, humidified, temperature controlled 5% $CO_2$ incubator, light and inverted microscopes, ELISA reader (450 nm filter), freezer, refrigerator scissors, forceps, stepper, pipettman 40-200 µl, pipettman 200-1000 µl, pipettman 5-40 µl, powerpette, sterile glass syringes and luer bridges.

Disposables

Cryotubes, 96-well enhanced binding ELISA plate (Nunc, Cat. #442404), 96-well non-sterile microtest plate (Falcon Cat. #3911), 24-well flat bottom steriled tissue culture plate (Nunc, Cat. #143982), petri dishes, Eppendorf tubes (polypropylene), steriled pipette tips 200-1000 µl, pipettes: 2, 5 & 10 ml, laboratory coat, gloves, 0.2µ cellulose acetate filter, filtered system 200 ml (Corning, Cat. #430767), Kim wipes, support platform, 10 ml syringes, 21 G×1½" needles, insulin syringes and combitips 5 ml.

Materials and Reagents

For the Immunization Procedure

95% ethanol (Bio Lab, Cat. #13680605, or equivalent), 70% ethanol prepared from 95% ethanol by dilution with distilled water, phosphate buffered saline (PBS)×1 (SIGMA, Cat. #3813, or equivalent), CFA containing 1 mg mycobacterium tuberculosis (MT) (H37Ra, ATCC 255177), (SIGMA, Cat. #F-5881, or equivalent), and GA RS batch.

For the In Vitro Bioassay Procedure

95% ethanol (Bio Lab, Cat. #13680605, or equivalent), 70% ethanol prepared from 95% ethanol by dilution with distilled water, trypan blue (BDH, Cat. #3407), DCCM1 (Defined Cell Culture Media) (Beit Haemek, Cat. #05-010-1A or equivalent), RPMI 1640 (Roswell Park Memorial Institute) (Beit Haemek, Cat. #01-100-1A), steriled L-glutamine 2 mM×100 (Bio Lab, Cat. #13.015), steriled MEM (Minimum Essential Media)—non-essential amino acids×100 (Bio Lab, Cat. #11.080), steriled sodium pyruvate 1 mM×100 (Bio Lab, Cat. #13.016), antibiotic/antimycotic Solution 1 (Bio Lab, Cat. #13.020), 2-mercaptoethanol (SIGMA, Cat. #M-7154), PBS (SIGMA, Cat. #3813), concavalin A (Con A) (SIGMA, Cat. #C-5275), MBP (Myelin Basic Protein) peptide (87-99) (BACHEM, Cat. #H-1964, or equivalent), and GA RS.

For the ELISA

IL-2 was measured by ELISA kit: OptEIA™ Set: mouse IL-2 (Pharmingen, Cat. #2614KI, or equivalent).

Animals

Female (SJLXBALB/C)F1 mice between 8-12 weeks old (Jackson Laboratories, Bar Harbor, Me.) were used, although female (BALB/C)F1 mice between 8-12 weeks old from other sources may be used. Animal housing and care conditions were maintained in specific pathogen-free (SPF) conditions.

Solutions

TABLE 1

| | Procedures for making solutions |
|---|---|
| Steriled PBS | The content of one package of PBS was dissolved in 1 liter double distilled water (ddH$_2$O). The buffer was filtered through a 0.2µ cellulose acetate filter and kept in refrigerator (2-8° C.) up to one week. |
| 2% (w/v) Trypan blue in PBS | About 0.5 g of Trypan blue were dissolved in 25 ml filtered PBS and stored in refrigerator up to 6 months. |
| 0.1% (v/v) Trypan blue in PBS | 0.1% Trypan blue solution was prepared from the 2% Trypan blue stock solution and filtered through a 0.2 µ cellulose acetate filter. The 0.1% Trypan blue solution was stored at room temperature for up to one month. |
| Steriled 2-Mercaptoethanol | 10 µl of 2-mercaptoethanol were added into 9.99 ml of sterilized PBS and filtered through a 0.2 µ cellulose acetate membrane and kept in refrigerator for up to 3 months. |
| GA RS stock solution of 1 mg/ml | About 10 mg of glatiramer acetate RS were weighed accurately and dissolved in ddH$_2$O to a concentration of approx and 1.2 mg/ml. The optical density (OD) of the RS solution was measured at 275 nm. The OD was adjusted to approx. 1.03 with ddH$_2$O, and a stock solution of 1 mg/ml of GA RS was obtained. The solution was mixed well, divided into working aliquots (200-500 µl) and stored at −20° C. until use. |
| Steriled MEM × 100 | The steriled solution was divided into aliquots of 5 ml each, and kept at −20° C. until use. After thawing, the working aliquot was kept in refrigerator for up to one month. |
| Antibiotic/antimycotic solution 1 | The original 20 ml package was kept at 20° C. The package was opened and all the contents were divided into aliquots of 2 ml each and stored at −20° C. until use. The working aliquot was stable and was able to be subjected to several freeze-thaw cycles. |
| Steriled L-glutamine 2 mM × 100 | The contents of the opened package were divided into aliquots of 2 ml each and kept at −20° C. until use. |
| Enriched DCCM1 medium | For 100 ml of sterile enriched DCCM1, the following components were mixed together: 1 ml of L-glutamine (2 mM), 1 ml MEM, 1 ml sodium pyruvate (1 mM), 200 µl antibiotic/antimycotic solution 1, 400 µl |

TABLE 1-continued

Procedures for making solutions

| | |
|---|---|
| | 2-mercaptoethanol and 96.4 ml DCCM1. The enriched DCCM1 was filtered through a 0.2 μ cellulose acetate filter and stored in refrigerator for up to 1 week. |
| MBP peptide | Primary bank: The stock solution of 10 mg/ml in ddH$_2$O was prepared, divided into working aliquots and kept at 20° C. Secondary bank: One aliquot of the primary bank (10 mg/ml) was thawed and diluted to 1 mg/ml with ddH$_2$O. The primary bank solution was divided into working aliquots of 50 μl each and kept at −20° C. Upon use, aliquot from the secondary bank was thawed and diluted with enriched DCCM1 to obtain a solution of 20 μg/ml. |
| Con A solution | Primary bank: The contents of one vial of 5 mg Con were dissolved in 1 ml PBS, mixed well and divided into aliquots of 50 μl each. The aliquots were kept at −20° C. up to the expiration date set by the manufacturer. Secondary bank: One aliquot of the primary bank (5 mg/ml) was thawed and diluted with 4.95 ml of enriched DCCM1 medium to obtain a solution of 50 μg/ml. The solution was divided into working aliquots of 100 μl each and kept at −20° C. Upon use, one aliquot from the secondary bank was thawed and diluted up to 1 ml (a 10-fold dilution) with enriched DCCM1 to obtain a solution of 5 μg/ml Con A. |

Immunization

GA RS emulsion in CFA was prepared under sterile conditions, i.e., in a laminar hood, using sterile equipment and materials.

Preparation of GA RS Solution

About 15 mg of GA RS were weighed accurately and dissolved in sterile PBS to a concentration of 5 mg/ml.

Preparation of GA RS Emulsion

Equal volumes of GA RS solution (5 mg/ml) and CFA were mixed. The mixture was transferred into a sterile glass syringe connected to a second glass syringe through a luer bridge. The mixture was mixed well by being transferred from one syringe to another until the mixture was well emulsified. A stable emulsion was confirmed when a drop of the emulsion floated on water without dispersing.

Injection

The GA RS emulsion was transferred into an insulin syringe. Then, 100 μl of the emulsion (250 μg GA per mouse) were injected into four footpads of each naive mouse (about 25 μl into each footpad). The immunized mice were used for the in vitro test 9-11 days following immunization.

Preparation of a Primary Culture of LN Cells

The primary culture of LN cells was prepared 9-11 days following immunization, according to the following procedure:

Surgical Procedure for Removal of LN Cells

The UV lamp was turned on 20 minutes before commencing work in the laminar hood and turned off when work began. Prior to placing any reagents under the hood, the working surface was cleaned with a 70% ethanol solution. Enriched DCCM1 medium was prepared. The enriched DCCM1 and the RPMI medium were pre-warmed at 37° C. prior to use. The mice were sacrificed by cervical dislocation. Each mouse was placed on its back and fastened to a support platform. The abdomen was sprayed with 70% alcohol and a middle incision was made (a 2 cm-long incision was usually sufficient). The skin was intersected towards the hind legs and LN was located from the hind and forelegs. The LN was transferred into a sterile petri dish containing about 5 ml sterile RPMI medium and the LN cells were teased out by a sterile syringe plunger. The sterile syringe was used to collect the cells' suspension from the petri dish (the collection of tissue debris was avoided by using sterile needles). The cells' suspension were transferred into a 50 ml sterile tube.

Cell Counting

Example Procedure for Counting LN Cells Derived from 5 Immunized Mice

The cells' tube were filled with RPMI medium up to 40 ml. The LN cells were centrifuged at 200×g for 10 minutes at room temperature (15-25° C.). The pellet was re-suspended with 40 ml RPMI. Two aliquots of 50 μl were drawn each from the cells' suspension diluted 4-fold with 150 μl of 0.1% Trypan blue in a microtest well. The aliquots were mixed well by pipetting gently up and down. The hemacytometer was covered with a cover slip. A 50-200 μl pipettman was used to load both aliquots into the upper and lower chambers of the hemacytometer, one suspension in each chamber. The mixture was allowed to settle within the chambers for about 2 minutes. Care was taken to not introduce bubbles into the chamber. The mixture (cell suspension+Trypan blue) was allowed to cover the entire surface of the chamber. If bubbles were present in the chamber, or if it was overloaded, the hemacytometer was cleaned completely and dried with wipes and the chambers were reloaded.

Figure 3:
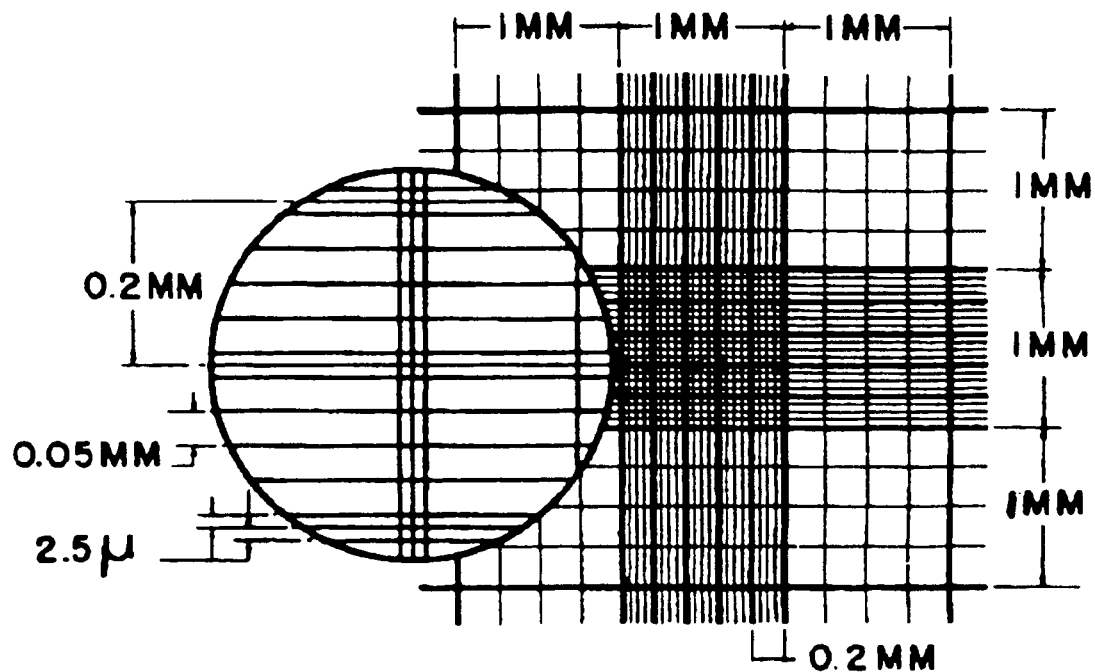
FIG. 3: Diagram of hemacytometer.

The viable cells were counted in the central square (composed of 25 large squares of 16 small squares each, see FIG. 3) of the upper and lower chambers. The viable cells did not absorb Trypan blue and were therefore characterized by a clear appearance. However, dead cells were permeable to Trypan blue and appeared blue in color. Cells appearing on the border of the central square were only counted if a portion of the cell was actually within the central square. If a cell was on the border, and not at all within the central square, it was not counted. The cells' density was calculated using the following equation:

$$\text{Average number viable cells(both chambers)} \times 4 \times 10^4 = \text{cells/ml.}$$

The cells were centrifuged at 200×g for 10 minutes at room temperature. The cells were re-suspended to a density of 1×10⁷ cells/ml with enriched DCCM1.

In Vitro Bioassay

The in vitro bioassay was performed in a 24-well, flat-bottomed tissue culture test plate at a final volume of 1 ml.

Preparation of GA RS Calibration Curve

One aliquot of the 1 mg/ml GA RS stock was thawed. The GA RS stock solution was diluted to 100 μg/ml (10-fold) with enriched DCCM1 medium and filtered through a 0.2μ cellulose acetate filter. Six serial dilutions of the GA RS solution with enriched DCCM1 medium were prepared between 2-50 μg/ml, as described by the example in Table 2.

TABLE 2

Example for preparation of GA RS dilutions

| GA RS CONCENTRATION (μg/ml) | VOLUME (μl) OF GA RS STOCK SOLUTION (100 μg/ml) | VOLUME (μl) OF ENRICHED DCCM1 |
|---|---|---|
| 50 | 1000 | 1000 |
| 30 | 600 | 1400 |
| 20 | 400 | 1600 |
| 10 | 200 | 1800 |
| 5 | 100 | 1900 |
| 2 | 40 | 1960 |

Preparation of GA DS Dilutions

About 10-20 mg of GA DS from the batch to be tested was weighed accurately and dissolved with ddH$_2$O to 1.2 mg/ml. The OD minus blank of the solution was measured at 275 nm. The OD of the sample was adjusted to approx. 1.03 with ddH$_2$O to obtain a stock solution of 1 mg/ml of GA. The stock solution of 100 μg/ml was prepared with enriched DCCM1 and filtered through a 0.2μ cellulose acetate filter. The stock solution was diluted to 10 and 20 μg/ml as described in Table 2 for the RS batch.

Assay Reaction

The following were added to the 24-well flat-bottomed tissue culture plate (see an example of a plate template below):

GA RS 0.5 ml of LN cells (final density, for example, 5×10⁶ cells/well).

0.5 ml of each GA RS dilution, thus the final concentrations of GA RS in the wells were 25, 15, 10, 5, 2.5 and 1 μg/ml.

GA DS Samples 0.5 ml of LN cells (final density, for example, 5×10⁶ cells/well).

0.5 ml of each sample dilution, thus the final concentrations of the test sample in the well were 5 and 10 μg/ml.

Each test included the following controls:

1) Negative control—LN cells incubated with a control peptide:

0.5 ml of LN cells (final density 5×10⁶ cells/well)

0.5 ml of MBP peptide solution (20 μg/ml) in enriched DCCM1 (final concentration 10 μg/ml)

2) Positive control—LN cells stimulated with Con A (non-specific T cell stimulant):

0.5 ml of LN cells (final density 5×10⁶ cells/well)

0.5 ml of Con A (5 μg/ml) in enriched DCCM1 (final concentration 2.5 μg/ml)

Example for a Plate Template

| GA RS* 1 μg/ml | GA RS* 2.5 μg/ml | GA RS* 5 μg/ml | GA RS* 10 μg/ml | GA RS* 15 μg/ml | GA RS* 25 μg/ml |
|---|---|---|---|---|---|
| Sample 1 5 μg/ml | Sample 1 10 μg/ml | | | | |
| Sample 2 5 μg/ml | Sample 2 10 μg/ml | | | | |
| Sample 3 5 μg/ml | Sample 3 10 μg/ml | | | Negative Control | Positive Control |

GA RS*—Glatiramer acetate reference standard.

The density of the cells was changed depending upon their response to GA. The cultures were kept at 37° C. in a humidified 5% CO$_2$ incubator for 18-21 hrs. The plate was centrifuged at 200×g for 10 minutes at room temperature. The supernatants were collected into cryotubes. The supernatants were divided into working aliquots to avoid repeated freezing/thawing of the samples. The supernatants were stored at −20° C. for up to one week. The hood was cleaned with 70% ethanol solution and dried with Kim wipes. The gloves were removed and the hands were immediately washed with disinfectant.

ELISA for IL-2 Detection

All samples were tested in triplicate. Each plate run included the following:

1) IL-2 standard curve—including at least 6 non-zero concentrations of IL-2.

2) Blank

+1$^{st}$ antibody, without IL-2 standard, +2$^{nd}$ antibody (zero point).

3) Samples

The culture media of GA RS, test samples and controls were diluted with enriched DCCM1 as follows:

a) A 2-fold dilution of the 1 and 2.5 μg/ml GA RS sample and of the negative control sample;

b) 5-10 fold dilutions of the 5-25 μg/ml GA RS samples and of the test samples; and c) 15-20 fold dilution of the positive control sample (Con A).

The ELISA protocol for measuring IL-2 levels was performed according to the manufacturer's recommendations. If the optical density of any sample reached the upper/lower limits of the plate reader, the sample was re-analyzed at a higher/lower dilution, respectively.

Calculations and Acceptance Criteria

ELISA Measurements

The mean absorbance was subtracted of the blank sample (zero IL-2 standard point) from the absorbance of standards, samples and controls and calculated for each set of triplicate the mean (absorbance-blank), standard deviation (SD), and relative standard deviation (RSD).

Sample Replicates

Whenever there was a suspected outlier, it was necessary to ensure that the outlier was statistically based, in order to elucidate any potential problems that may have affected the overall results. If the RSD between triplicate measures was higher than 10% and the average OD-blank was >0.300, outlier rejection was applied using the Dixon Q-Test. The Dixon Q-Test was used to reject possible outliers when the relevant acceptance criteria was not satisfied in a test based on replicates. The outlier test was applicable only to replicate measurements of the same standard solution. For less than 10 observations, only 1 outlier was able to be determined and eliminated. This procedure expanded the use of the Dixon Q-Test in rejecting outliers from any number of replicate measurements between 3 and 7, with a confidence level of 95%.

Procedure

The suspected outlier was designated $X_1$. All other measurements were labeled in reference to the suspected outlier, e.g., $X_2$ was the value next to the suspected outlier, $X_3$ was second value from the suspected outlier, $X_k$ was the farthest from the suspected outlier and $X_{k-1}$ was the value second from the farthest, etc.

For 3-7 replicates, the following equation was used:

$$\frac{X_2 - X_1}{X_k - X_1}.$$

The appropriate k value was determined from the calculated fraction using Table 3.

TABLE 3

| No. of Observations (k) | k Value<br>Value at $P_{95}$ |
|---|---|
| 3 | 0.94 |
| 4 | 0.76 |
| 5 | 0.642 |
| 6 | 0.560 |
| 7 | 0.507 |

If no outlier was identified by the Dixon Q-Test but the % difference between 2 out of the 3 replicates was not more than 10%, the closest 2 replicates were used for calculating the % potency. Otherwise, the ELISA test was repeated for this sample. Outlier rejection from samples with OD<0.300 (blank, negative control and low standard points) was applied. When an outlier was located, when it was rejected and reported. Duplicate measures were used for the calculation of % potency.

Blank Samples

The absorbance of each of the blank samples was ≦10% of the mean absorbance of the highest concentration of the IL-2 standard. If one of the blank replicates was beyond the above limits, it was rejected and duplicate samples were used.

IL-2 Standard Curve

The IL-2 standard curve was graphed according to the manufacturer's recommendations. IL-2 standards that exhibit poor sensitivity or sample processing error were able to be rejected if a minimum of six non-zero concentration IL-2 standards remained in the curve. The back-calculated standard concentration had a relative error (RE) greater than 20% for the lower calibration point and ±15% for all other concentrations. The IL-2 calibration curve was constructed from at least six non-zero concentration points (at least 17 calibration points), covering the range of expected concentrations. The standard curve range was able to be truncated if the high or low concentrations failed. The $R^2$ of the linear regression curve was ≧0.97.

Assay Controls

The concentration of IL-2 was calculated in all samples from the linear regression plot of the IL-2 standard, utilizing the equation of the linear regression curve. The final concentration of IL-2 was calculated in all samples by multiplying by the samples' dilution factor.

Negative Control (MBP Peptide)

The final concentration of IL-2 in at least 2 out of the 3 replicates of the negative control sample was below the levels of IL-2 measured for the lowest calibration point of the GA RS curve.

Positive Control (Con A)

The final concentration of IL-2 in at least 2 out of the 3 replicates of the positive control sample was similar to or above the level of IL-2 in the highest calibration point of the GA RS curve.

Calculation of the Relative Potency of GA DS Batches

GA RS Curve

The GA RS curve was plotted on a log-log scale, with log IL-2 concentration on the y-axis and log GA RS concentration on the x-axis. The calibration curve was constructed from at least five non-zero concentrations (at least 14 calibration points). Calibration points were rejected as described for the IL-2 standard points. The best-fit regression curve was computed through the standard points. The $R^2$ was ≧0.97. The slope ($\beta$) was ≧0.77.

Parallelism Analysis

The dose-response curve of each test sample was plotted on a log-log scale, with log IL-2 concentration on the y-axis and log GA DS concentration on the x-axis. The best fit regression curve was computed through the sample points. The slope ($\beta^*$) was within the following range:

$$\beta \times 0.635 \leq \beta^* \leq \beta \times 1.365.$$

If $\beta^*$ was out of limits, the in-vitro test was repeated in duplicate (two separate sample preparations). If $\beta^*$ in one re-test failed, the batch was rejected. If $\beta^*$ in both re-tests was within limits, the % potency and 95% fiducial limits were determined.

Estimation of the % Potency and the Fiducial Limits

The estimate of the random error to be used to determine the Fiducial Limits (which have a 95% probability of including the "true % potency") was obtained by using ANOVA. This statistical technique splits the total variation between observed responses into separate components, namely:

$$\left.\begin{array}{l}\text{1. due to linear dose-response}\\\text{2. due to the mean effect of preparation}\end{array}\right\} \text{Model}$$

$$\left.\begin{array}{l}\text{3. due to deviation from parallelism}\\\text{4. due to deviation from linearity}\\\text{5. due to residual between-replicate variation}\end{array}\right\} \begin{array}{l}\text{Random}\\\text{Error}\end{array}$$

The components 3 and 4 were included in the random error term due to non-significant deviations from linearity and parallelism, respectively. The total sum of squares was partitioned into 3 components (SS-Regression, SS-Preparation and SS-Error), the appropriate number of degrees of freedom and the F-test for significance.

The % potency of the tested batch was calculated and the 95% fiducial limits for the estimated potency as described below:

Computational Algorithm for the Calculation of Relative Potency and 95% Fiducial Limits Step 1: Compute the Transformation of the Given Date (GA. Batch and GA. RS.) into $\text{Log}_{10}$ Scale:

$Y_{k1} = \log_{10}(\text{response}_{k1})$; $i=1, \ldots n_k$ $X_{k1} = \log_{10}(\text{dose}_{k1})$; $i=1, \ldots, n_k$ where k=1, 2 is a preparation index of GA. batch and GA. RS, respectively;

$n_1$ and $n_2$ are the total numbers of measurements performed for the GA. batch and GA. RS, respectively.

Thus, $N=n_1+n_2$ is an overall total number of observations.

Step 2: Calculate the Common Slope for the Linear Regression Based on all Measured Data Points Via the Formula:

$$\beta = \frac{\sum_{j=1}^{N}(Y_j - \overline{Y})\cdot(X_j - \overline{X})}{\sum_{j=1}^{N}(X_j - \overline{X})^2};$$

where $\overline{Y}$ is an overall mean value of $\log_{10}$(response);

$\overline{X}$ is an overall mean value of $\log_{10}$(dose).

Step 3: Calculate the Sum of Squares Due to Regression on $\log_{10}$(Dose) as:

$$SS_{REG} = \beta^2 \cdot \sum_{j=1}^{N}(X_j^i - \overline{X})^2;$$

Step 4: Calculate the Random Error Sum of Squares as:

$$SS_{ERR} = \sum_{k=1}^{2}\sum_{i=1}^{n_k}[Y_{ki} - \overline{Y}_k - \beta\cdot(X_{ki} - \overline{X}_k)]^2;$$

where $\overline{Y}_k, \overline{X}_k$ are mean $\log_{10}$(response) and $\log_{10}$(dose) values, respectively, of preparation k.

Step 5: Calculate the Mean Square Error Term as Following:

$DF_{ERR}$(random error degrees of freedom)×N−3;

$MS_{ERR}=SS_{ERR}/DF_{ERR}$.

Step 6: Use the Statistical Tables of t-Distribution in Order to Find the Appropriate Value of t-Statistic:

$t=t(0.975, DF_{ERR})$.

Step 7: Calculate the Point Estimate of the Relative Potency as Following:

$$\% \text{ Potency} = 10^{\frac{\overline{Y}_1-\overline{Y}_2}{\beta}-(\overline{X}_1-\overline{X}_2)} \cdot 100\%;$$

Step 8: Calculate the Expression Denoted by C Via the Formula:

$$C = \frac{SS_{REG}}{SS_{REG} - MS_{ERR}\cdot t^2};$$

Step 9: Calculate the Logarithms of Lower and Upper Limits of 95% Fiducial Interval:

$$\text{Log}_{10}(\text{Lower Limit}) = C\cdot\frac{\overline{Y}_1-\overline{Y}_2}{\beta} - (\overline{X}_1-\overline{X}_2) - \frac{\sqrt{MS_{ERR}\cdot C}\cdot t}{\beta}\cdot\sqrt{\frac{1}{n_1}+\frac{1}{n_2}+\frac{(\overline{Y}_1-\overline{Y}_2)^2}{SS_{REG}-MS_{ERR}\cdot t^2}};$$

$$\text{Log}_{10}(\text{Upper Limit}) = C\cdot\frac{\overline{Y}_1-\overline{Y}_2}{\beta} - (\overline{X}_1-\overline{X}_2) + \frac{\sqrt{MS_{ERR}\cdot C}\cdot t}{\beta}\cdot\sqrt{\frac{1}{n_1}+\frac{1}{n_2}+\frac{(\overline{Y}_1-\overline{Y}_2)^2}{SS_{REG}-MS_{ERR}\cdot t^2}};$$

Step 10: Transform the Values Computed in the Previous Step into Original Scale by Taking of Anti-Logarithms of the Resulting Log-Limits and Multiply by 100%.

The estimated potency of GA DS batch was not less than 80% and not more than 125% of the stated potency. The fiducial limits of error (P=0.95) of the estimated potency were less than 70% and not more than 143% of the stated potency. If the batch was outside the above limits, the in-vitro test was repeated in duplicate. If the results of both re-tests were within specifications, the batch was acceptable. If one re-test failed, the batch was rejected.

Documentation

The LN cell count and ELISA plates template were recorded. The original ELISA reader records and the result form were filed.

Example 2

Development of Standard Procedure of Example 1

Experiment 2A: Profile of Cytokines Secreted from GA RS-Specific T Cells

The LN cells were derived from female (SJL×BALB/C)F1 mice immunized with 250 µg GA RS in CFA 9-11 days earlier were cultured in the presence of various concentrations of GA RS. The cells were incubated with GA RS for 18-24 hours at 37° C. in a 5% $CO_2$ humidified incubator. Subsequently, the cultures were centrifuged and the supernatants collected and assayed for cytokines by ELISA.

The ELISA was performed using biotinylated antibodies specific to the cytokine and strepavidin-horseradish peroxidase (HRP) conjugated for detection. Each plate ran included blank control (first and second antibodies without the cytokine standard). Each plate ran also included quality control (QC) samples (three concentrations of cytokine standard within the assay's linear range). Each in vitro test included a positive control (Con A, a non-specific T-cell stimulant) and a negative control (no GA or any other antigen). All the cytokines were measured after 18-24 hours of incubation. Levels of TGF-β, IL-10 and IL-4 were tested again after 72 hours of incubation. The results are shown in Table 4.

TABLE 4

| Cytokine profile | |
| --- | --- |
| Cytokine | Secretion levels |
| IL-2 | ++ |
| INF-γ | ++ |
| IL-6 | + |
| L-10 | + |
| L-13 | − |
| TGF-β | − |

TABLE 4-continued

Cytokine profile

| Cytokine | Secretion levels |
|---|---|
| IL-4 | − |
| TNF-α | − |

In Table 4, the maximal levels measured for each cytokine are presented in arbitrary units: (−) <detection limit; (+) up to ~400 pg/ml; and (++) >400 pg/ml. Table 4 shows that in response to GA RS in culture, the LN cells secreted IL-2, INF-γ, IL-10 and IL-6, while TNF-α, IL-4, IL-13 and TGF-β were not detected in the culture media. These results indicate that the cytokines produced by the GA RS-specific T cells are of $Th_0$ type. It should be noted that a $Th_0$ profile was observed in different immunization protocols, i.e., immunization with IFA or with low doses of GA.

Since IL-2 is a good marker for T cell activation, and since the secretion of IL-2 in response to GA RS was very reproducible, with a linear dose-response relationship, IL-2 seemed to be the optimum cytokine to measure T cell activation.

Experiment 2B: Optimization of the Immunization Procedure

Figure 4:
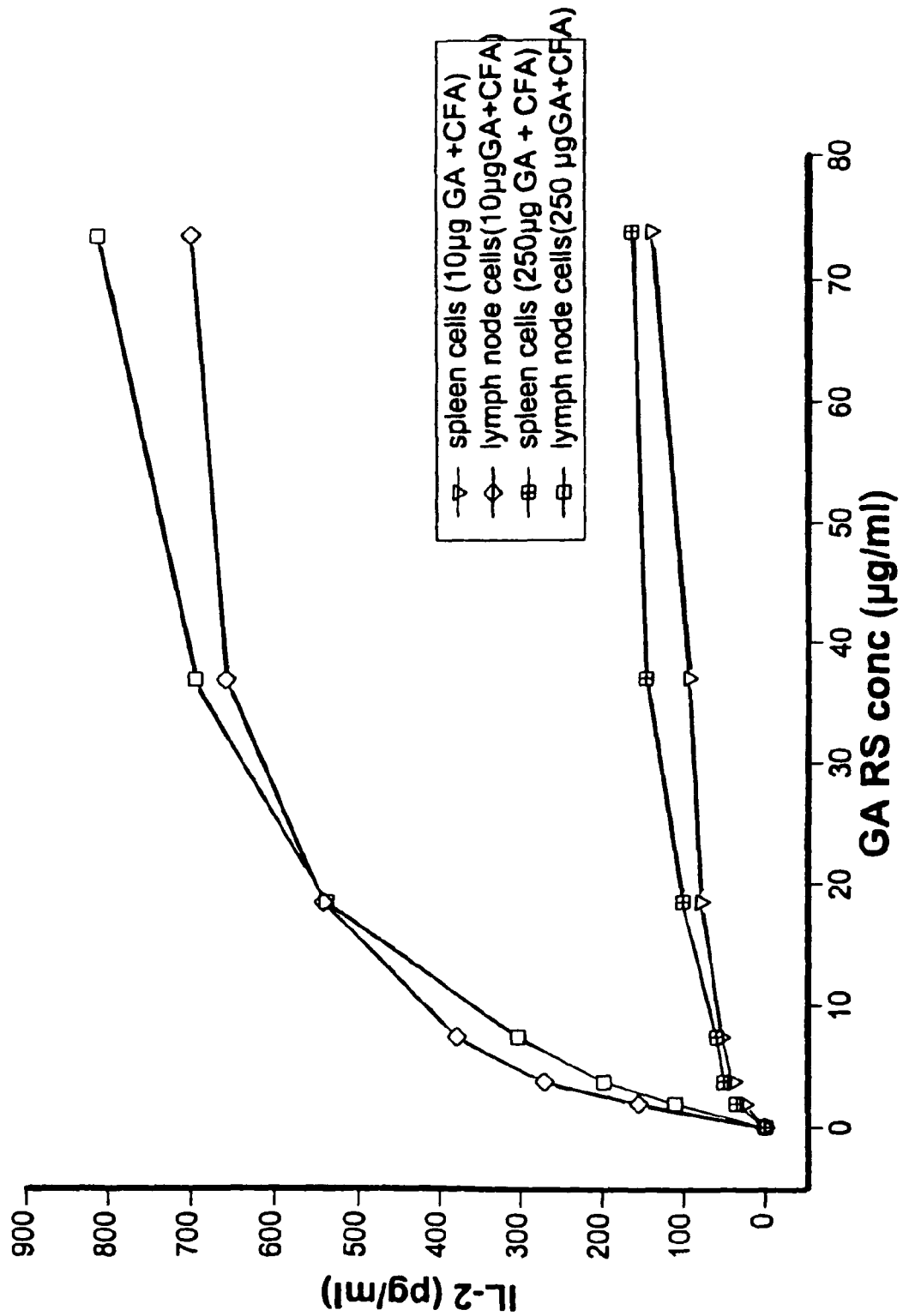
FIG. 4: Optimization of the immunization protocol—culture source and GA Reference Standard (RS) dose effect. Primary cultures of Lymph Node (LN) and spleen cells were derived from mice immunized with 10 or 250 μg GA RS+complete Freund's adjuvant (CFA). The cells were cultured in the presence of increasing concentrations of GA RS. Following overnight incubation at 37° C., the culture media were collected and assayed for IL-2 by enzyme-linked immunoabsorbent assay (ELISA).

Several experiments were performed to establish the optimal immunization protocol. The first experiment tested the effect of GA RS (immunizing antigen) dose on T-cell responses in the LN and in the spleen. Two groups of 10 mice each were immunized with either 250 μg GA in CFA (group 1) (as in the EAE blocking test) or with 10 μg GA in CFA (group 2). Primary cultures were prepared from both the LN and the spleens of the immunized mice. The cultures were incubated overnight with various doses of GA RS and afterwards the culture media were collected and assayed for IL-2 as in Experiment 2A. The results in FIG. 4 clearly show that in both immunization protocols the levels of IL-2 secreted from LN cells are high compared to those secreted from spleen cells. Based on these results it was decided to use primary cultures of LN cells for the assay. In addition, the doses of GA RS injected into mice did not affect the T cell response in culture. Both LN and spleen cells secreted similar quantities of IL-2 regardless of the immunizing dose of GA RS. This indicates that the immunization procedure is robust, and that even major variations in the immunizing dose of GA RS do not affect the immunological outcome.

Figure 5:
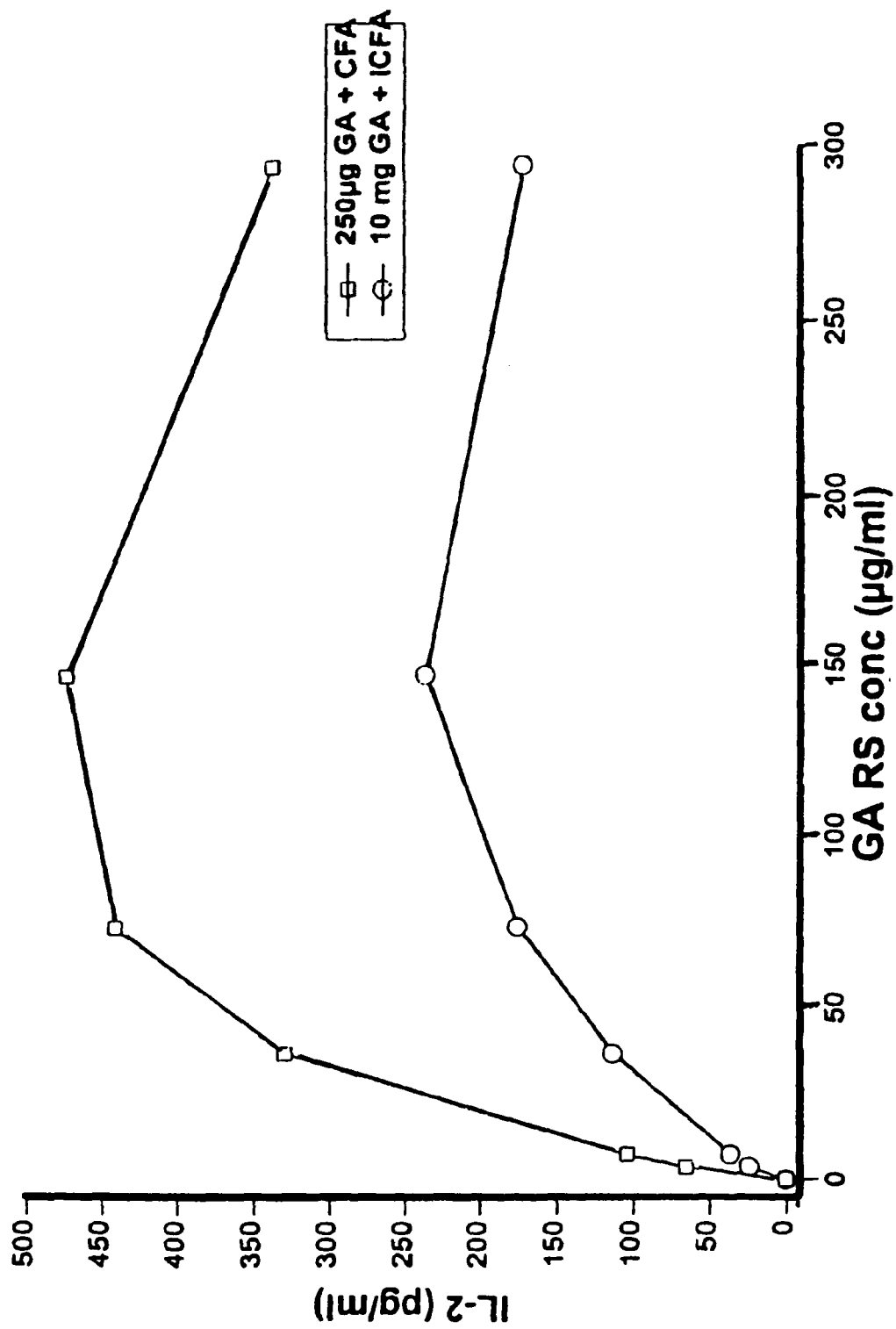
FIG. 5: Optimization of the immunization protocol—adjuvant and dose effect. Primary cultures of LN cells derived from mice immunized with 250 μg GA RS+CFA or with 10 mg GA RS+incomplete Freund's adjuvant (ICFA) were cultured in the presence of increasing concentrations of GA RS. Following overnight incubation at 37° C., the culture media were collected and assayed for interleukin-2 (IL-2) by ELISA.

For further optimization of the immunization protocol, one group was injected with 250 μg GA RS in CFA and the second group with 10 mg GA in ICFA. The dose of GA RS in the second group was higher since ICFA, a weaker adjuvant, was used. Ten days later, the response of the LN cells from both groups to GA RS was tested in vitro. FIG. 5 shows that immunization with 250 μg GA RS in CFA induced a much stronger response in culture, although a much lower dose of antigen was used.

Based on these findings, and on the fact that 250 μg/mouse of GA in CFA is very effective in blocking EAE (at least 80% blocking of EAE in this mouse strain), 250 μg/mouse of GA in CFA appears to be the optimum dose.

Figure 6:
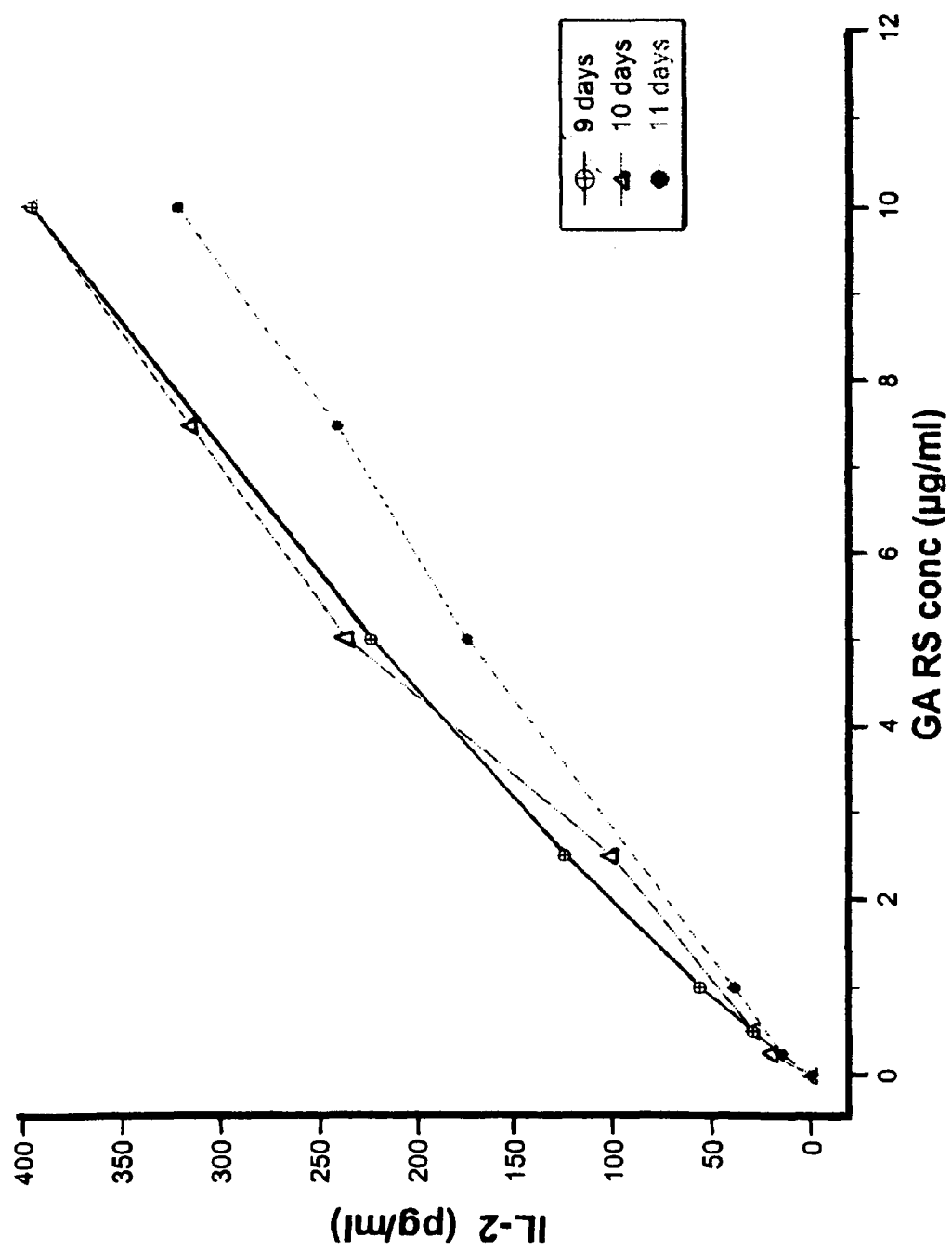
FIG. 6: Effect of the immunization period. Mice were immunized with 250 μg GA RS in CFA and LN were removed after 9, 10 and 11 days. The response of the LN cells from different groups to various concentrations of GA RS was tested in vitro by measuring IL-2 secretion by ELISA.

Specific T cells were usually generated within approximately 10 days, following a single immunization with CFA. FIG. 6 shows the response of the LN cells to GA RS in culture, prepared 9, 10 and 11 days following immunization. Since the dose-response of IL-2 secretion was similar on all days, the immunization period may last for 9-11 days.

Experiment 2C: Optimization of the In Vitro Test Conditions

Several experiments were performed to establish the optimal protocol for the in-vitro reaction. These studies included optimization of culture conditions, incubation time, stability of IL-2 in test samples and stability of GA RS at −20° C.

i) Culture Media

Cultures of mouse lymphoid cells are usually maintained in RPMI medium, supplemented with 1% normal mouse serum. Normal mouse serum may contain endogenous IL-2 that can be detected by the anti mouse IL-2 monoclonal antibodies used in the ELISA kit. In addition, the use of different lots of normal serum may increase the inter-day variations of the in vitro test. To avoid cross-contamination with endogenous mouse IL-2, and to reduce the inter-day variations of the method, the responses of the GA-specific T cells were tested in 4 different culture media: 1) RPMI+1% normal mouse serum (NMS); 2) RPMI+1% fetal bovine sera (FBS) (bovine IL-2 is not recognized by the anti mouse IL-2 used in the ELISA kit); 3) Biotarget (serum-free media produced exclusively by BeitHaemek, Israel); and 4) DCCM1 (serum-free media produced by various manufacturers).

Figure 7:
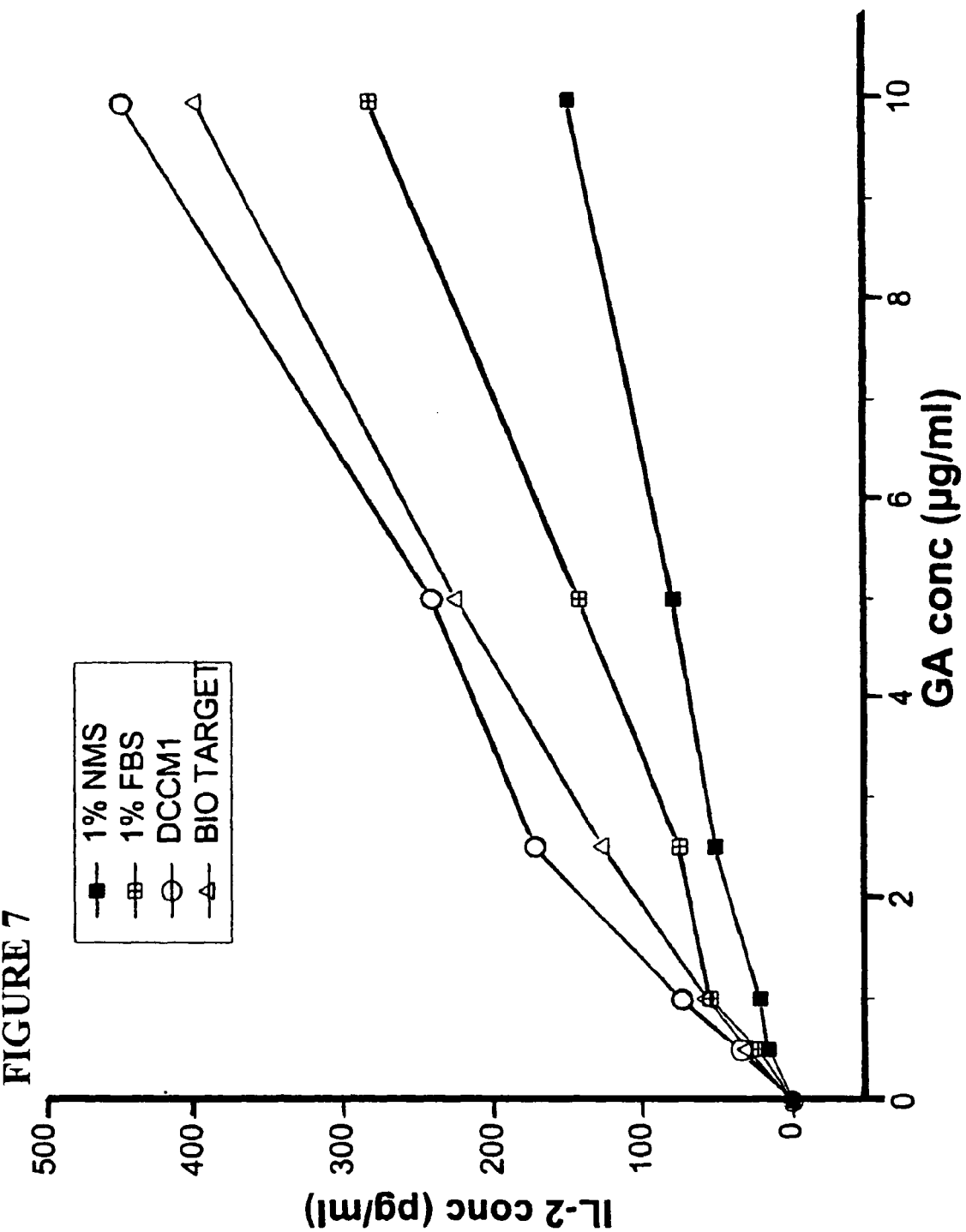
FIG. 7: Effect of the culture media on GA-specific T cell response. Primary cultures of LN cells were cultured with different media containing either 1% normal mouse serum (NMS), 1% fetal bovine serum (FBS) or defined cell culture media (DCCM1) The cells were incubated with increasing concentrations of GA RS for 21 hours at 37° C. Subsequently, the culture media were collected and assayed for IL-2 by ELISA.

FIG. 7 shows the results of a representative experiment that compares the response of LN cells to GA RS in different culture media. The best responses were observed when serum-free media were used. The dose-response range was left-shifted in the absence of serum. This can be explained by previous studies showing that GA binds to albumin and to other serum proteins. This binding may reduce the availability of GA in culture to interactions with APCs, and thus higher concentrations of GA are required to stimulate the T cells. Based on these results, the optimum medium seems to be DCCM-1 medium.

ii) Kinetics of IL-2 Secretion

IL-2 is an autocrine and paracrine growth factor that is essential for clonal T-cell proliferation and for functional properties of B cells and macrophages. Following stimulation of the culture with GA RS, IL-2 is secreted by the activated GA-specific T cells and is subsequently consumed by the LN cells. Kinetic studies of IL-2 secretion were performed in an attempt to determine the optimal (peak) time for collection of the supernatants, following stimulation with GA. LN cells were cultured and incubated with various concentrations of GA RS at 37° C. in a humidified $CO_2$ incubator. At the intervals indicated in FIG. 8, aliquots were sampled and the cells were removed by centrifugation. The supernatants were kept at 20° C. and at the end of the experiment were assayed for IL-2 by ELISA.

Figure 8:
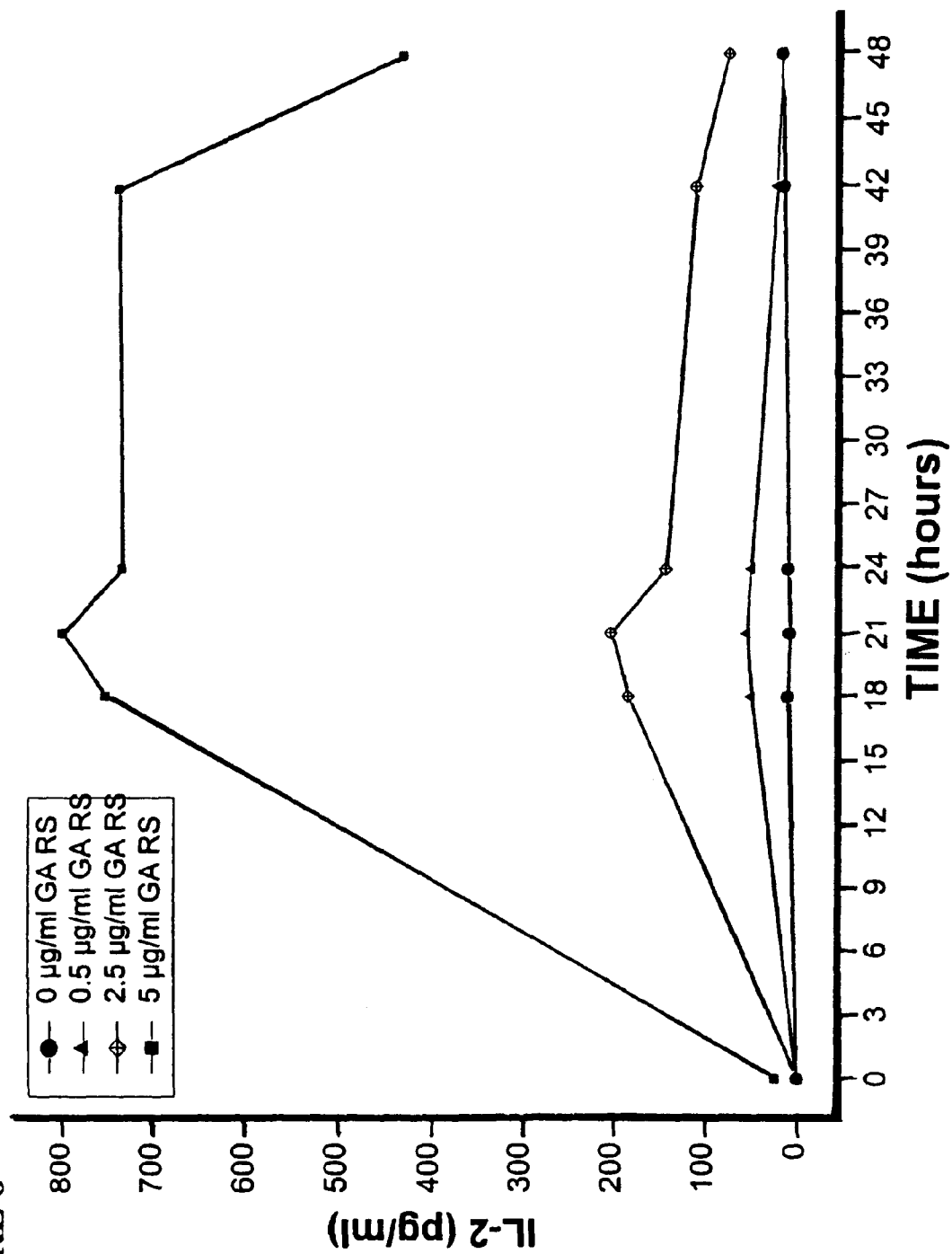
FIG. 8: Kinetics of IL-2 secretion in response to GA RS. A primary culture of LN cells was prepared from mice immunized with 250 μg GA RS+CFA. The cells were incubated with 0, 0.5, 2.5 and 5 μg/ml GA RS at 37° C. for the indicated intervals. At each time point, an aliquot of $5 \times 10^6$ cells was centrifuged and the supernatant was kept at −20° C. All samples were assayed simultaneously for IL-2 by ELISA.

FIG. 8 shows that the peak of IL-2 levels in the culture media is between 18-21 hours. The reduction in IL-2 levels in samples collected from 24-48 hours can be explained by the consumption of IL-2 by the LN cells. Thus, the optimum time for supernatant collection appears to be after 18-21 hours of incubation.

iii) Measurement of Cytokines

The method relies on accurate measurements of IL-2 in samples of GA RS and test samples. During the experiments, the levels of IL-2 were measured by OptEIA (Pharmingen, Cat. #2614KI)—an ELISA kit specific for mouse IL-2. This ELISA kit is very sensitive and the results are accurate and reproducible.

iv) Stability of IL-2 in Test Samples at −20° C.

Figure 9:
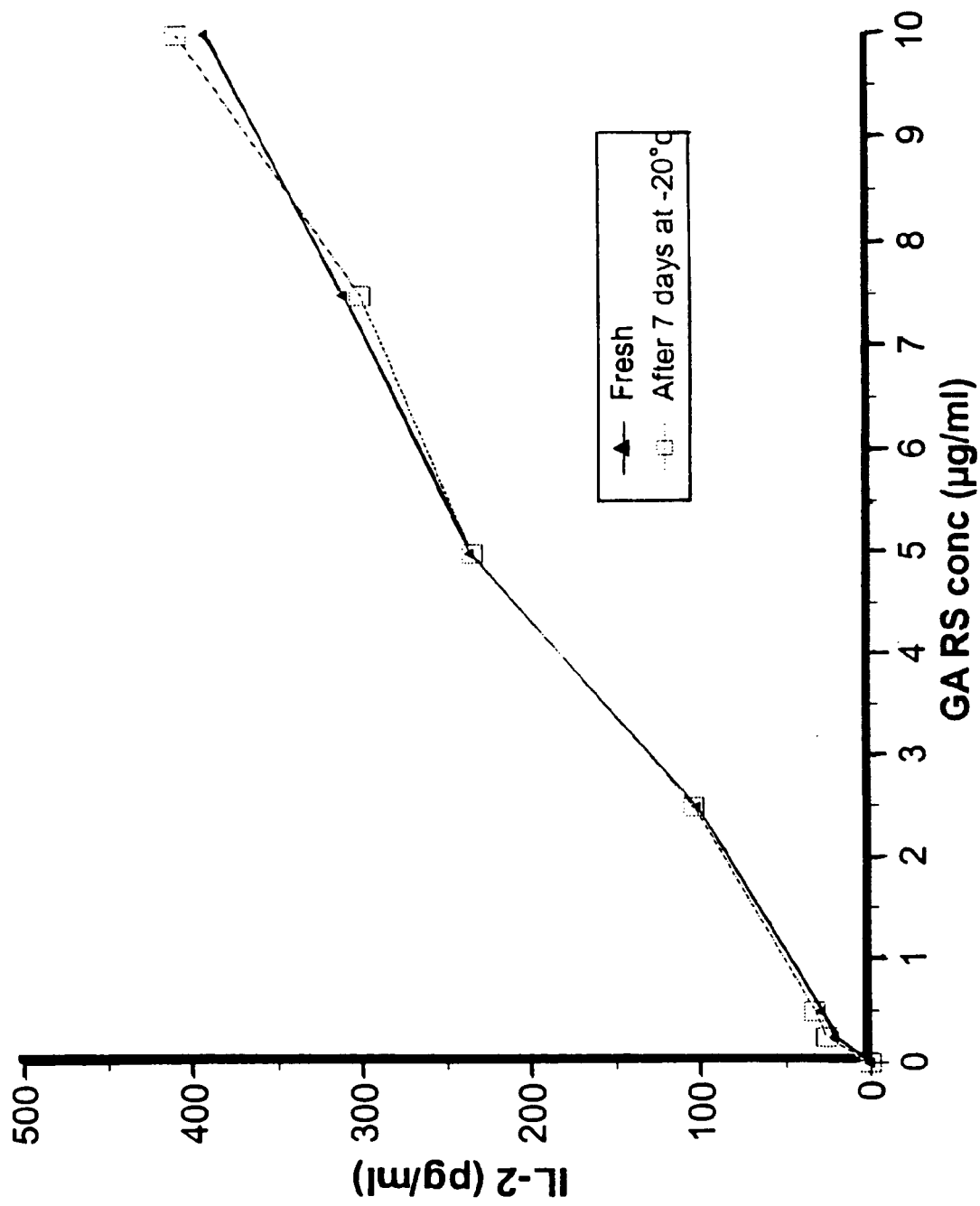
FIG. 9: Stability of IL-2 in culture media. A primary culture of LN cells was prepared from mice immunized with 250 μg GA RS+CFA. The cells were incubated with various concentrations of GA RS at 37°. After overnight incubation, the supernatants were collected and divided into two aliquots. One aliquot was assayed immediately by ELISA, and the second was kept for 7 days at −20° C. prior to being assayed.

In most of the experiments performed, the culture media were collected and kept at −20° C. before being analyzed by the ELISA. Preliminary studies of the stability of IL-2 in culture media show that the cytokine is stable for one week at −20° C. (FIG. 9). Therefore, the culture media of the in-vitro test samples can be kept at −20° C. for up to one week prior to measuring IL-2. The results of this experiment also demonstrated that the ELISA results are very reproducible—the levels of IL-2 measured in the samples were practically identical in two ELISA plate runs performed on two different days one week apart.

v) Stability of GA RS Solution at −20° C.

Figure 10:
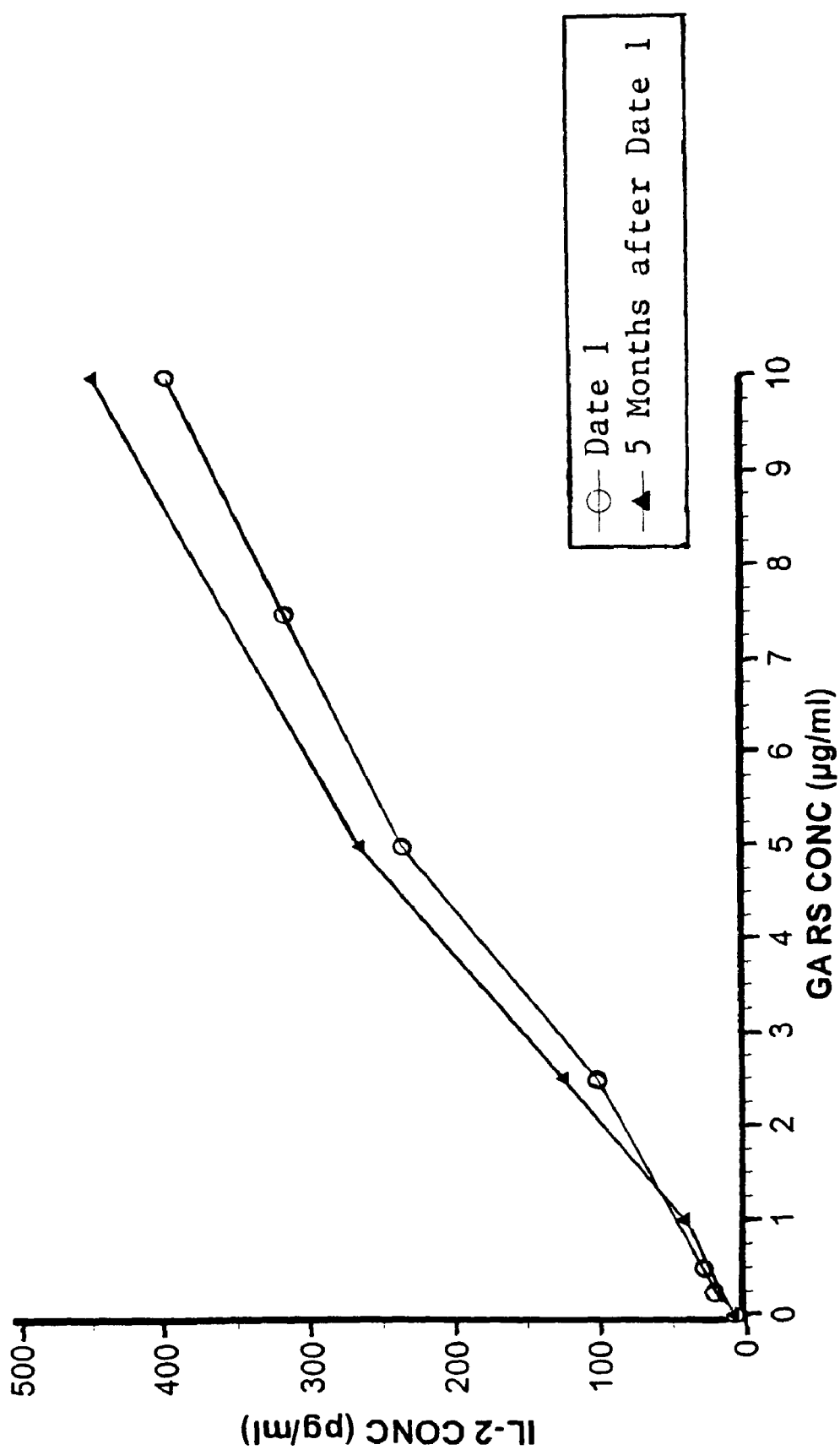
FIG. 10: Stability of GA RS solution at −20° C. GA RS solution of 1 mg/ml was prepared, divided into aliquots and kept at −20° C. The dose-response of the GA-specific cells to GA RS solution was tested at time zero (Date 1) and after 5 months at −20° C.

To test the stability of GA RS solution at −20° C., the dose-response of a GA RS solution was tested immediately following preparation, and after storage for 5 months at −20° C. FIG. 10 shows that there is practically no difference in the dose-response curves of GA RS solution before and after storage for 5 months at −20° C. Therefore, aliquots of GA RS solution can be prepared and kept at −20° C. for at least 5 months before use.

Experiment 2D: Determination of Linear Range of GA RS Calibration Curves

The statistical validation was carried out based on GA RS calibration curves calculated and evaluated separately for each one out of 21 plates received for the analysis. These 21 samples were gathered at different times over an approximately four-month period. The GA concentration range for the given plates varied from 0.25 to 50 µg/ml. The following validation characteristics derived from the GA RS calibration curves constituted the main concern of the analysis:

1. Optimal transformation to ensure wider limits of the linear range;
2. Determination of the linear range limits;
3. Overall criteria for accepting a calibration curve;
4. Estimation of assay accuracy and precision;
5. Assessment of duplicate reliability (see the paragraph below).

The nature of the experiments was such that there were typically 3 replicates (triplicates) at each calibration point. However, in some instances, when a triplicate measurement could not be provided, the assessment of duplicate reliability became essential.

Linearity of GA Dose-Response Relationship

The basis of most aspects of the validation discussion presented below was a linear regression model that related the IL-2 concentration (pg/ml) to the GA concentration (µg/ml). The assumption of the linearity of this relationship was necessary for the appropriate fitting of the linear regression model. The data was plotted in a Linear-Linear scale. The same relationship was transformed into Log-Log scale, as well as a Log-Linear scale, and a Log-Square Root scale. The Log-Log transformation demonstrated the most suitable linear features. Thus, the chosen form of the regression model was the Log-Log one:

$$\mathrm{Log}_{10}(IL\text{-}2\ \mathrm{conc}) = a + \beta * \mathrm{Log}_{10}(GA\ \mathrm{conc}) + \mathrm{error}$$

The response variable was a log-transformed mean of the 3 replicates measured at each calibration point. This model was fitted to each calibration sample and the appropriate statistics ($R^2$, intercept, and slope) were calculated for each fitted curve. The value of $R^2$ reflected the ratio of the residual sum of squares (RSS) to the total sum of squares (TSS) via the formula:

$$R^2 = 1 - \mathrm{RSS}/\mathrm{TSS}$$

Linear Range Determination

The linear range was determined based on the following criteria:

1. Visual inspection of plotted $\log_{10}$ (IL-2 conc) vs. $\log_{10}$ (GA conc);
2. The regression influence diagnostics, such as Cook's known in the art distance statistic;
3. Evaluation of the variation of the precision and accuracy values calculated for the calibration curves for several potential linear range definitions provided a visual evaluation of the linearity of the relationship. There was no evidence of non-linearity of the relationship inside of the chosen linear range 1-25 µg/ml.

Experiment 2E: Determination of Criteria for GA RS Standard Curve

Validation parameters derived from GA RS calibration curves, fitted within selected limits (1-25 µg/ml) of the linear range, were determined to be the following:

1. $R^2$ of the linear regression fits of $\log_{10}$ (IL-2 conc) to $\log_{10}$ (GA conc) for each plate in the study;
2. Slopes and intercepts for these straight line fits;
3. Accuracy calculated at each calibration point for each plate; and
4. Precision calculated at each calibration point for every plate.

In order to compute accuracy and precision, each calibration curve was used to calibrate (back-calculate) the GA Concentrations given the values of IL-2 concentration:

$$X_{i\text{-}back} = 10^{(\log_{10}(IL\text{-}2\ Conc)_i - \alpha/\beta)}$$

i=1, 2, 3–triplicate index.

The basic measure of (in)accuracy used was the percent difference between the mean of the estimates of concentration and the true concentration in the triplicate samples:

$$\mathrm{inaccuracy} = ([\mathrm{Mean}(X_{i\text{-}back}) - GA\ \mathrm{conc.}]/GA\ \mathrm{conc.}) * 100\%.$$

The basic measure of precision used was the relative standard deviation (RSD or CV) of the triplicate estimates of concentration:

$$\mathrm{precision} = CV(X_{i\text{-}back}) = [\mathrm{Std.\ Dev.}(X_{i\text{-}back})/\mathrm{Mean}(X_{i\text{-}back})] * 100\%.$$

The goal of the analysis was to propose acceptance criteria for the fitted calibration curve which ensured that the accuracy and precision of the method were adequate. The acceptance criteria were based on the $R^2$ and the slope of the GA RS calibration curve. About 80% of the plates could be characterized by small inaccuracy values (<13%) and by good precision (1.1%-6.7%). For these 16 "well behaved" standard curves, the following results were obtained:

1. High $R^2$ values (>0.98);
2. Relatively high slope values, reflecting dose response relationships (>0.78 in 15 of 16 plates).

Since the majority of calibration curves were characterized by relatively high $R^2$ (mean=0.99) and by relatively steep slopes (mean=0.87), in contrast to the excluded plates which had both relatively low $R^2$ (mean=0.94) and rather flat slopes (mean=0.72), the overall acceptance criteria for calibration curves were considered in terms of $R^2$ and slope. The simple rule defining the acceptance parameters was based on the computation of cut-off points for the slope and $R^2$ separately and located them mid-way between the maximum value for rejected curves (max_$R^2$=0.95 max_slope=0.77) and the minimum value for accepted curves (min_$R^2$=0.98 min_slope=0.77). Thus, the acceptance criteria were derived as follows:

1. $R^2 \geq 0.97$;
2. Slope $\geq 0.77$.

These criteria were applied to at least five different (triplicate) concentrations for fitting the calibration curve within the range 1-25 µg/ml of GA concentration. Additionally, the range of intercept values was between 1.42-1.78, mean=1.58. This range was similar for the 16 eligible and the 5 removed plates.

Accuracy and precision were calculated for each curve, and for each concentration among those on the plate. These individual values (for each curve and concentration) were also averaged over:
1. Different concentrations for each curve;
2. Different curves for each concentration; and
3. Over all curves and concentrations.

The relevant conclusion was that for GA RS calibration curves based on at least five different calibration points in the linear range 1-25 µg/ml, when the calibration curve was restricted to having $R^2 \geq 0.97$ and slope $\geq 0.77$, the resultant average accuracy and precision was estimated as:
1. The mean (±SD) accuracy value for the method was: 8.0%±2.3%; and
2. The mean (±SD) precision value for the method was: 2.9%±1.7%.

Reliability Assessment of GA RS Calibration Curves Based on Duplicate Measurements A comparison of the assay's accuracy and precision descriptive statistics was performed in order to assess the reliability of GA RS calibration curves fitted using duplicate measurements at each calibration point. In addition, the individual accuracy and precision values (for each curve and concentration) for all three possible selections of duplicate measurements, out of the given triplicate, were studied. When concentrating on those curves that satisfied the acceptance criteria described in the previous section and fitted within the limits of the defined linear range 1-25 µg/ml, it was evident that when a triplicate measurement can not be provided for some reasons, it can be successfully substituted by duplicate measurement.

extension of the proof for the case where $\beta^* < \beta$ is obvious). The back-calculated dose value, for a given log(response) was:

$$X_{back} = 10^{(Y-\alpha)/\beta} \text{ where } Y = \log_{10}(\text{IL-2 concentration}).$$

The formula for the (in)accuracy calculation was:

$$(\text{in})\text{accuracy} = [(10^{(Y-\alpha)/\beta} - X_{true})/X_{true}] * 100\%.$$

$Y_{low}$ and $Y_{high}$ were the lowest and highest log(response) values permitted by the highest allowable (in)accuracy of ±12.6%.

Thus, the region where the hypothesis of the equality of slopes was to be accepted was:

$$\begin{cases} [(10^{(Y_{low}-\alpha)/\beta} - X_1)/X_1] * 100\% \geq -12.6\% \\ [(10^{(Y_{high}-\alpha)/\beta} - X_2)/X_2] * 100\% \leq -12.6\% \end{cases}$$

$$\begin{cases} 10^{(Y_{low}-\alpha)/\beta}/X_1 \geq 0.874 \\ 10^{(Y_{high}-\alpha)/\beta}/X_2 \leq 1.126 \end{cases}$$

Thus, the boundaries of the equality of the slopes were:

$$\begin{cases} Y_{low} = \alpha + \beta \cdot \log(X_1 \cdot 0.874) \\ Y_{high} = \alpha + \beta \cdot \log(X_2 \cdot 1.126) \end{cases}$$

TABLE 5

Accuracy and Precision Descriptive Statistics Summary

| | Triplicate | | Duplicate (1, 2) | | Duplicate (1, 3) | | Duplicate (2, 3) | |
|---|---|---|---|---|---|---|---|---|
| | Accuracy | Precision | Accuracy | Precision | Accuracy | Precision | Accuracy | Precision |
| Mean | 8.00 | 2.93 | 8.13 | 2.53 | 7.98 | 2.88 | 8.40 | 2.40 |
| S.D. | 2.31 | 1.72 | 2.80 | 1.66 | 2.45 | 2.13 | 2.79 | 1.53 |
| Min | 5.23 | 1.10 | 4.93 | 0.95 | 5.21 | 0.93 | 4.97 | 0.81 |
| Max | 12.79 | 6.67 | 12.51 | 6.33 | 12.44 | 9.24 | 13.41 | 5.99 |

The mean (±SD) accuracy and precision of the method based on triplicates were 8.0%±2.3% and 2.9%±1.7%, respectively (Table 5).

The mean (±SD) accuracy and precision of the method based on duplicates were:
1. Accuracy: 8.1%±2.8%; Precision: 2.5%±1.7%;
2. Accuracy: 8.0%±2.5%; Precision: 2.9%±2.1%; and
3. Accuracy: 8.4%±2.8%; Precision: 2.4%±1.5%.

Experiment 2F: Determination of Statistical Relationship

It was found that the mean (in)accuracy of the method is 8.0% with SD=2.3%. The aim was to develop a reliable test for the slope comparison of two log(dose)-log(response) lines of a new GA batch vs. GA RS. The test took into account the (in)accuracy of the above-mentioned method. The highest limit of the approximate 95% individual tolerance region for the mean (in)accuracy of the method served as a threshold value: Mean+2*SD=12.6%. Thus, variations within the range±12.6% were considered non-significant.

A full mathematical explanation of the relationship between $\beta^*$ (the slope of the batch line), $\beta$ (the slope of the standard line) and the highest permitted (in)accuracy value follows. Without loss of generality, only the case where $\beta^* > \beta$ will be proved in detail (due to the existing symmetry, the The slope of a straight line was calculated as follows:

$$\beta^* = (Y_{high} - Y_{low})/(\log X_2 - \log X_1) = [\beta \cdot \log([X_2/X_1] \cdot [1.126/08.74])]/\log(X_2/X_1)$$

$$\beta = [\beta \cdot \log(1.288)]/\log(X_2/X_1) = \beta \cdot (1 + \log(1.288)/\log(X_2/X_1))$$

Assuming for the particular case under consideration that $X_2/X_1 = 2$ (for dose levels of 5 and 10 µg/ml), $\beta^*$ was calculated as follows:

$$\beta^* = \beta \cdot (1 + \log(1.288)/\log 2) = \beta \cdot 1.365$$

Combining this result with the one obtained for the symmetric case where $\beta^* < \beta$, the limits were calculated as:

$$\begin{cases} \beta^* \leq \beta \cdot 1.365 \\ \beta^* \geq \beta \cdot 0.635 \end{cases}$$

In the given data, all slope values were within the matching critical limits, meaning that no deviation from the parallelism assumption was observed.

Once a batch was accepted as statistically valid (existence of linearity and parallelism has been proved), the potency ratio of the test preparation relative to the standard was estimated. This was done in a parallel line assay by fitting straight parallel lines to the data and determining the horizontal distance between them:

$$M = \log \rho = \frac{\overline{Y}_T - \overline{Y}_S}{B} - (\overline{X}_T - \overline{X}_S);$$

where $\rho$ denoted the potency, $\overline{Y}_S, \overline{Y}_T, \overline{X}_S, \overline{X}_T$ were the mean log(responses) and log (doses) of the standard and test preparations, respectively. B—was a common slope for the standard and test log(dose)-log(response) lines. The least-squares estimate of the common slope—B was a weighted average of the least-squares estimates of two slopes separately from the standard line and the test line. Taking the anti-logarithm of the expression above, one was able to obtain a point estimate of the "true % potency" of a test preparation relatively to its standard:

$$\text{Potency} = 10 \frac{\overline{Y}_T - \overline{Y}_S}{B} - (\overline{X}_T - \overline{X}_S) \cdot 100\%.$$

Example 3

Validation of the Standard Procedure of Example 1

The goal of the analysis, presented below, was to establish validated release specifications for the relative potency of a GA batch. A GA batch was considered valid, if the following criteria, based on statistical inference, were fulfilled:
1. No violations of the assumptions involved in the bioassay analysis approach:
    (a) Independence and normality of the log(responses);
    (b) Homogeneity of the variance of the log(responses);
    (c) No outliers;
    (d) Parallelism (non-significance of the slope ratio test);
2. The point estimate of the relative potency was within a pre-specified range: 80%-125%; and
3. The 95% Fiducial Limits for the "true relative potency" value were within a wider pre-defined confidence range: 70% to 143%.

The model assumed that the standard and the test preparations should behave as if one were a simple dilution of the other. This means that the log(dose)-response lines for the two preparations should not deviate significantly from linearity and parallelism. Thus, an anti-logarithm of the constant horizontal displacement between these straight lines was able to serve as an estimate of the potency ratio. These two requirements, linearity and parallelism, constituted a concept of the assay validity. The check of validity was a prerequisite to the estimation of the relative potency and its fiducial limits.

The estimate of random error was needed for the computation of fiducial limits for the true value of the relative potency. This measure was obtained by the implementation of the statistical technique known as "Analysis of Variance" (ANOVA). Therefore, the classical statistical assumptions of the ANOVA must have been satisfied. The requirements for the statistical analysis of a parallel-line bioassay model were as follows:
1. The responses were independently normally distributed about their expected values;
2. The variance of the response was not affected by the mean response value;
3. There were no outliers;
4. The relationship between the log(dose) and response was able to represented by a straight line over the range of doses; and
5. The straight line of the test preparation was parallel to that of the standard.

The batch analysis data was obtained from different experiments performed on different days by different operators. Validation trials of the standard procedure of Example 1 were carried out by a series of experiments, each involving: 1) immunization of mice with 250 µg GA RS in CFA; 2) preparation of a primary culture from the LN cells 9-11 days following immunization; 3) incubation of the LN cells with various concentrations of GA RS and with test samples; 4) collection of the culture media and analysis of IL-2 levels by ELISA; 5) plotting a GA RS curve based on triplicate IL-2 measurements performed at 6 dose levels from 1-25 µg/ml; and 6) comparison of the T cell response to each test sample to the response to the RS batch (in triplicate) at two concentrations within the linear range (5 and 10 µg/ml). The % CV was also calculated for each triplicate in order to detect any problems associated with variability between triplicates (normally, the % CV between triplicates should not exceed 10-15%). For the given data, no violations of the conditions were detected.

The validation characteristics used to provide an overall knowledge of the capabilities of the analytical procedure were: linearity, range, accuracy, precision, specificity and robustness. The validation criteria and analyses were based on the ICH consensus guideline, "Validation of Analytical Procedures: Methodology", November 1996 (CPMP/ICH/281/95). Statistical methods recommended in "European Pharmacopoeia" guideline were adapted to the given data for analysis purposes.

Experiment 3A: Linearity and Range

In each in vitro test, a dose-response curve of GA RS batch was used to calculate the relative response of the cells to the tested samples. Each calibration curve included at least five points (without zero). Twenty-one calibration curves collected from different in vitro tests, performed during the development and the validation stages, were plotted and evaluated for each plate.

Statistical analysis of the data revealed that the plots of $\log_{10}$ (IL-2 concentration) versus $\log_{10}$ (GA RS concentration) provided the best linear fit. The linear range mainly emerged by visual inspection and evaluation of accuracy and precision of the calibration points. The % RSD was calculated for each triplicate in order to detect any problems associated with variability between triplicates (normally, the % RSD between triplicates should not exceed 10-15%). The range of GA RS curve was specified between 1-25 µg/ml.

Based on these analyses, the GA RS curve should be comprised of at least 6 calibration points, one with zero concentration (negative control) and at least 5 concentrations of GA RS in the range between 1 and 25 µg/ml. Linear regression of $\log_{10}$ (IL-2 concentration) versus $\log_{10}$ (GA RS concentration) should have an $R^2 \geq 0.97$ and a slope $\geq 0.77$.

Experiment 3B: Accuracy

The accuracy of the method was established across the specified linear range of the GA RS curve. Statistical analysis of the data revealed that the mean accuracy of the method was: 8.0%±2.3%.

Experiment 3C: Precision

The basic measure of precision used was the relative standard deviation (RSD) of replicate (usually triplicate) estimate of concentration.

The RSD was established across the linear range of GA RS curves. Statistical analyses of the data revealed that the mean precision of the method was 2.9%±1.7%. The reliability of duplicate measures was equivalent to that of triplicate. Therefore, when one of the three replicates was identified as an outlier, the outlier was omitted and the results from duplicate measures were accepted.

Experiment 3D: Method Repeatability

The GA specific T cell response to a GA DS batch was measured repeatedly, 3 times, in the same in vitro test. Three weights of the same batch were each diluted to 5 and 10 µg/ml and incubated with the GA-specific T-cells. The levels of IL-2 in the culture media of the test samples and of the GA RS samples, were measured by ELISA in triplicate. The % potency and 95% fiducial limits of the cells to each replicate were calculated relative to the GA RS. Table 6 shows the % response calculated for each replicate.

TABLE 6

Method Repeatability

| Sample # | GA DS conc. (µg/ml) | % Potency | | | AVG N = 6 | SD | RSD | 95% Fiducial Limits (Lower Limit-Upper Limit) |
|---|---|---|---|---|---|---|---|---|
| 1 | 5 | 75 | 80 | 74 | 77 | 3.3 | 4.2 | 67-89 |
|   | 10 | 73 | 79 | 81 |  |  |  |  |
| 2 | 5 | 83 | 83 | 92 | 84 | 5.0 | 5.9 | 73-97 |
|   | 10 | 80 | 79 | 88 |  |  |  |  |
| 3 | 5 | 72 | 74 | 71 | 76 | 5.2 | 5.2 | 65-88 |
|   | 10 | 80 | 78 | 79 |  |  |  |  |

Experiment 3E: Intermediate Precision

The % response of a GA DS batch was tested in 3 different in vitro tests, performed in different days, by 3 different investigators from the same laboratory. Table 7 summarizes the % potency and 95% fiducial limits determined for this batch in the 3 repeated experiments.

TABLE 7

Intermediate Precision

| Test # | GA DS conc. (µg/ml) | % Potency | | | AVG N = 6 | SD | RSD | 95% Fiducial Limits (Lower Limit-Upper Limit) |
|---|---|---|---|---|---|---|---|---|
| 1 | 5 | 85 | 86 | 83 | 83 | 3.1 | 3.7 | 71-97 |
|   | 10 | 77 | 84 | 84 |  |  |  |  |
| 2 | 5 | 90 | 86 | 87 | 86 | 3.0 | 3.7 | 79-94 |
|   | 10 | 82 | 84 | 89 |  |  |  |  |
| 3 | 5 | 75 | 80 | 74 | 77 | 3.3 | 4.2 | 65-88 |
|   | 10 | 73 | 79 | 81 |  |  |  |  |

Experiment 3F: Method Reproducibility

The reproducibility of the method was assessed by means of inter-laboratory study. The % response GA DS batch was tested in two different experiments, performed in 2 different laboratories, using different analysts, equipment and reagents. Table 8 summarizes the results from both labs.

TABLE 8

Method Reproducibility

|  | Lab 1 | Lab 2 |
|---|---|---|
| Avg % Potency ± RSD | 86 ± 3.5 | 83 ± 5.0 |
| %95 Fiducial Limits | 79-94 | 78-90 |

Based on the above experiments, it can be concluded that the in vitro test is reproducible.

Experiment 3G: Specificity

The discrimination of the method was tested at 3 levels: 1) discrimination between samples incubated with/without GA RS (matrix effect); 2) discrimination between GA RS and other related and non-related proteins and peptides, including GA DS; and 3) discrimination between GA RS and GA related copolymers in which the peptide sequences have been deliberately modified.

i) Recognition of GA RS by GA RS-Specific T Cells (Matrix Effect)

GA-specific T cells were induced by immunization of female (SJL×BALB/C)F1 mice mouse with 250 g GA RS in CFA. This dose of GA is routinely used for testing the biological activity of GA batches in this mouse strain using the EAE blocking test. The control group in this experiment was injected with CFA alone. Ten days following immunization, LN cells were removed from the both groups of mice. The cells were incubated with GA RS for 18-24 hours at 37° C. in a 5% $CO_2$ humidified incubator.

Figure 2:
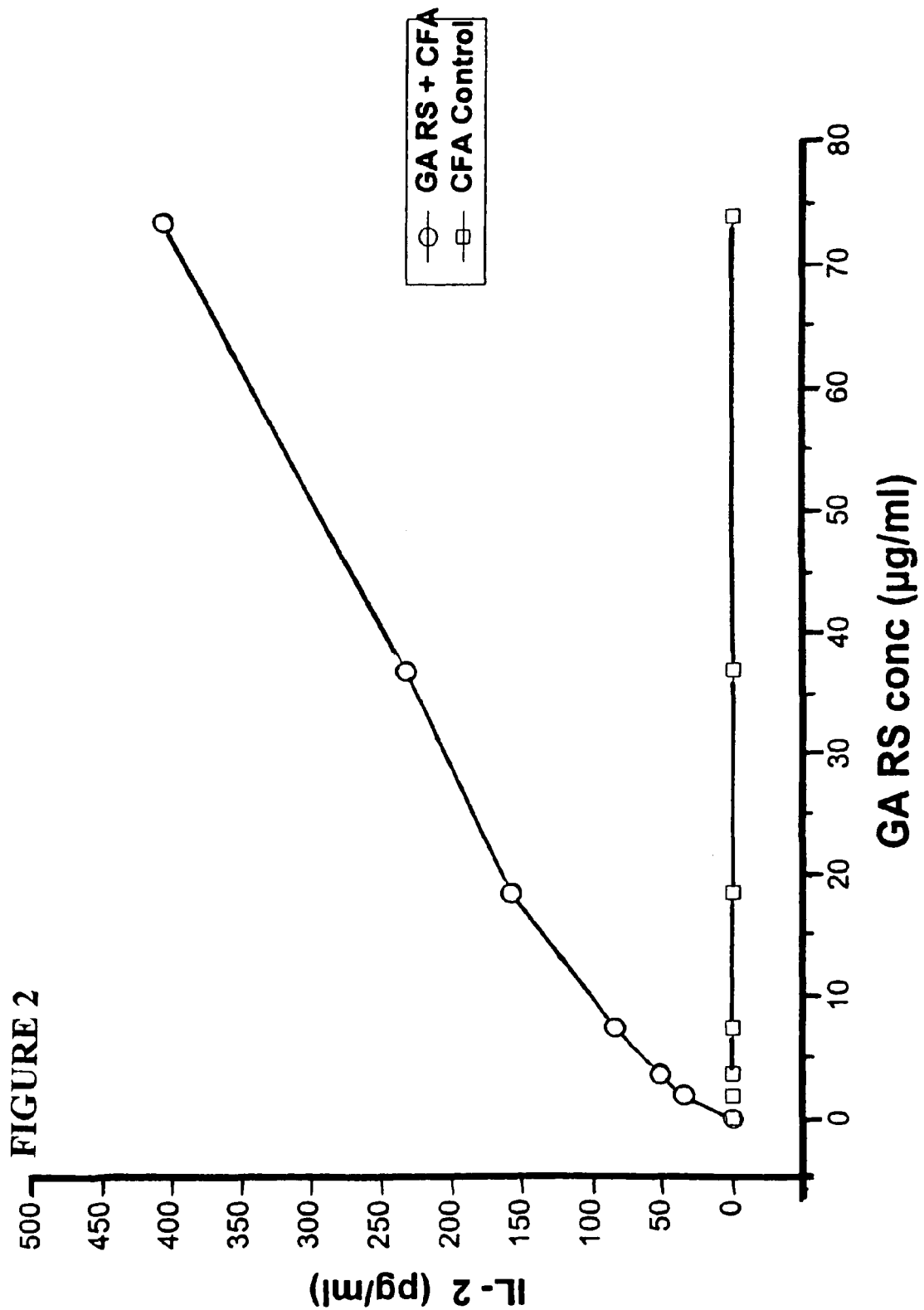
FIG. 2: Induction of GA-specific T cells. Primary cultures of LN cells derived from mice immunized with 250 μg GA RS+CFA or with CFA alone were cultured in the presence of increasing concentrations of GA RS. Following overnight incubation at 37° C. the culture media were collected and assayed for IL-2 by ELISA.

Subsequently, the cultures were centrifuged and the supernatants collected and assayed for interleukin-2 (IL-2, a cytokine secreted from activated T cells) by ELISA using biotinylated antibodies specific to IL-2 and strepavidin-horseradish peroxidase (HRP) conjugate for detection (FIG. 1). Each plate run included blank control (first and second antibodies without the cytokine standard). Each plate run also included quality control (QC) samples (three concentrations of cytokine standard within the assay's linear range). Each in vitro test included a positive control (Con A, a non-specific T-cell stimulant) and a negative control (no GA or any other antigen). FIG. 2 shows that the LN cells from mice immunized with GA RS secrete IL-2 dose dependently in response to GA RS in culture, while LN cells from the control mice do not respond to GA RS in culture. The levels of IL-2 in the negative control samples is usually below or close to the ELISA detection limit (approximately 3 pg/ml). These IL-2 levels are always below the levels secreted by the lowest calibration point of GA RS (1 µg/ml). These results indicate that the secretion of IL-2 by the GA specific T-cells is GA dependent.

ii) Discrimination Between Related and Non-Related Antigens

The discrimination between related and non-related antigens (proteins and single peptides) was demonstrated by testing the response of the GA RS-specific T cells to various antigens in-vitro. A primary culture of LN cells derived from female (SJL×BALB/C)F1 mice immunized 9-11 days earlier with 250 µg GA RS in CFA. The primary culture was incubated overnight with GA RS and with various other antigens at 37° C. in a 5% $CO_2$ humidified incubator. Then, the cultures were centrifuged and the supernatants collected and assayed for IL-2 by ELISA as in Experiment 3G(i).

Table 9 shows that in this experimental system the GA-specific T cells did not respond to either human MBP (myelin basic protein), the MBP immunodominant peptide pp. 87-99 (an encephalitogenic peptide), or its analog pp. 87-99$_{Ala\ 96}$ (an EAE suppressor peptide). Lysozyme, a non-relevant basic protein, was also not recognized by the GA-specific T cells. TV-35 and TV-109 were peptides with a molecular weight of 3757 and 11727, respectively (PCT International Publication No. WO 00/18794). These peptides had a defined sequence comprised from the same four amino acids of GA (Ala, Glu, Lys, Tyr), in the same molar ratio as in GA. The GA RS-specific LN cells did not respond to TV-35, and had a very low cross-reactivity with TV-109. These results can be explained by the observation that immunization with GA RS induced the formation of a mixture of T cells with different specificity towards the multiple T-cell epitopes present in GA. TV-35 and TV-109 may share common sequences with GA, however, and incubation of the GA-specific T cells with a single peptide probably caused only a partial stimulation of a small fraction of the GA-specific cells in culture. Thus, the overall T-cell response (secretion of IL-2) was below or close to detection limits.

TABLE 9

Specificity of GA RS-specific LN cells

| Antigen | % Potency[1] |
|---|---|
| GA RS | 100 |
| Lysozyme | 0 |
| Human MBP | 0 |
| MBP pp. 87-99 | 0 |
| MBP pp. 87-99$_{Ala\ 96}$ | 0 |
| TV-35 | 0 |
| TV-109 | 17 |

Figure 11:
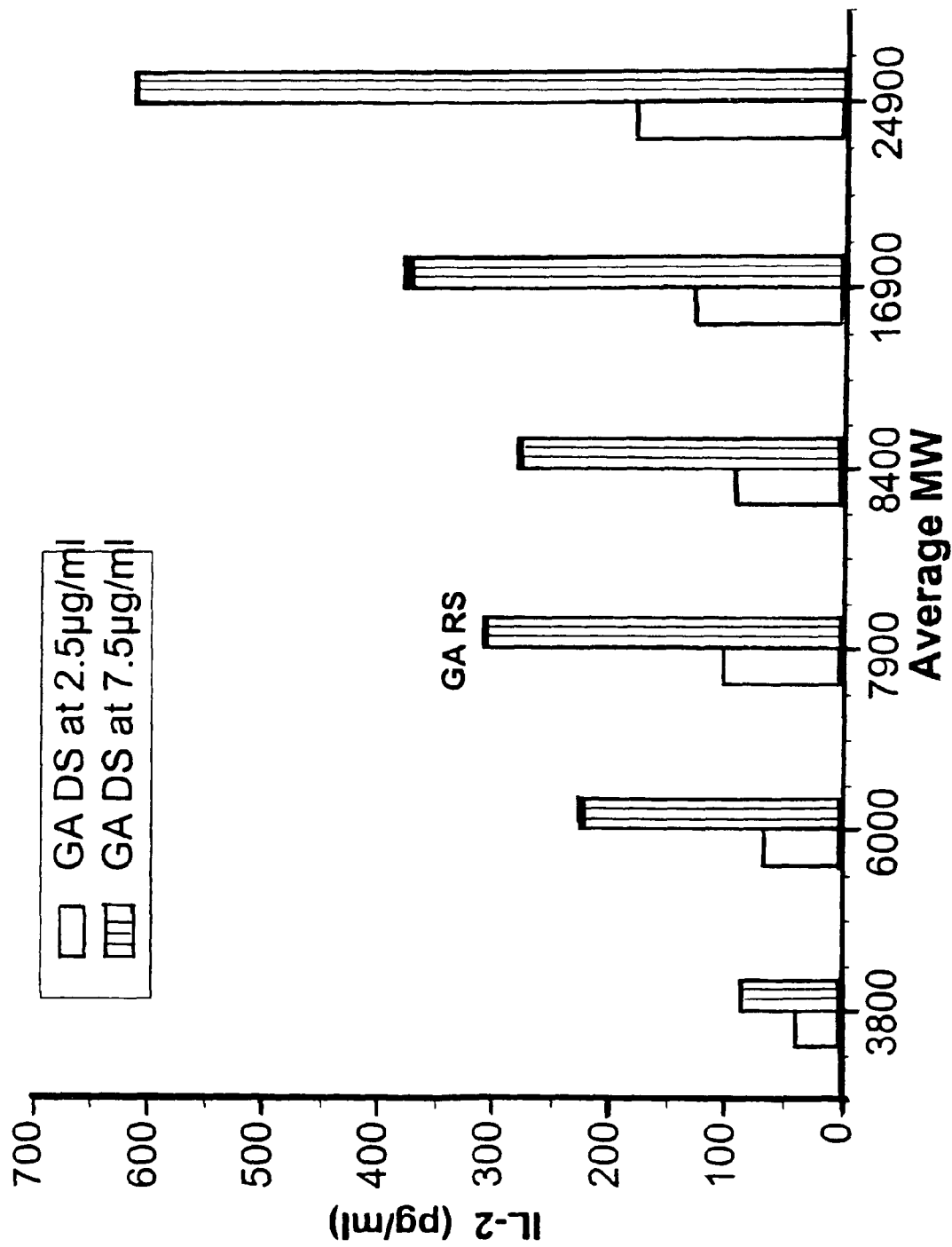
FIG. 11: Effect of the average molecular weight (MW) on the GA RS-specific T-cell response. A primary culture of LN cells was prepared from mice immunized with 250 μg GA RS+CFA. The cells were cultured in the presence of 2 different concentrations of GA RS and of GA Drug Substance (DS) of different molecular weights. Following overnight incubation at 37° C. the culture media were collected and assayed for IL-2 by ELISA.

[1] % Potency = $\dfrac{\text{IL-2 concentration in culture media of the antigen} \times 100}{\text{IL-2 concentration in culture media of GA RS}}$ The in vitro test was sensitive to the average molecular weight (MW) of the GA batch. FIG. 11 shows the response of the GA RS-specific cells to GA RS (MW=7900) and to GA DS batches differing in their average MW. As can be seen, the response generally correlated with the average MW; the higher the average MW, the greater the response. However, it should be noted that the release specifications for the average MW of GA DS are between 4700-10000, and that similar levels of IL-2 were secreted in response to DS batches with average MW within specifications (FIG. 11). These results indicate that the method was highly specific to GA and sensitive to changes in the average MW of GA.

iii) Recognition of GA Drug Substance (DS) and Copaxone® Drug Product (DP) by GA RS-Specific T Cells Nine to eleven days following immunization of female (SJL×BALB/C)F1 mice with 250 μg GA RS in CFA, the LN cells were removed and cultured with various doses of GA RS batch (the immunizing antigen) and with a DS batch.

Figure 12A:
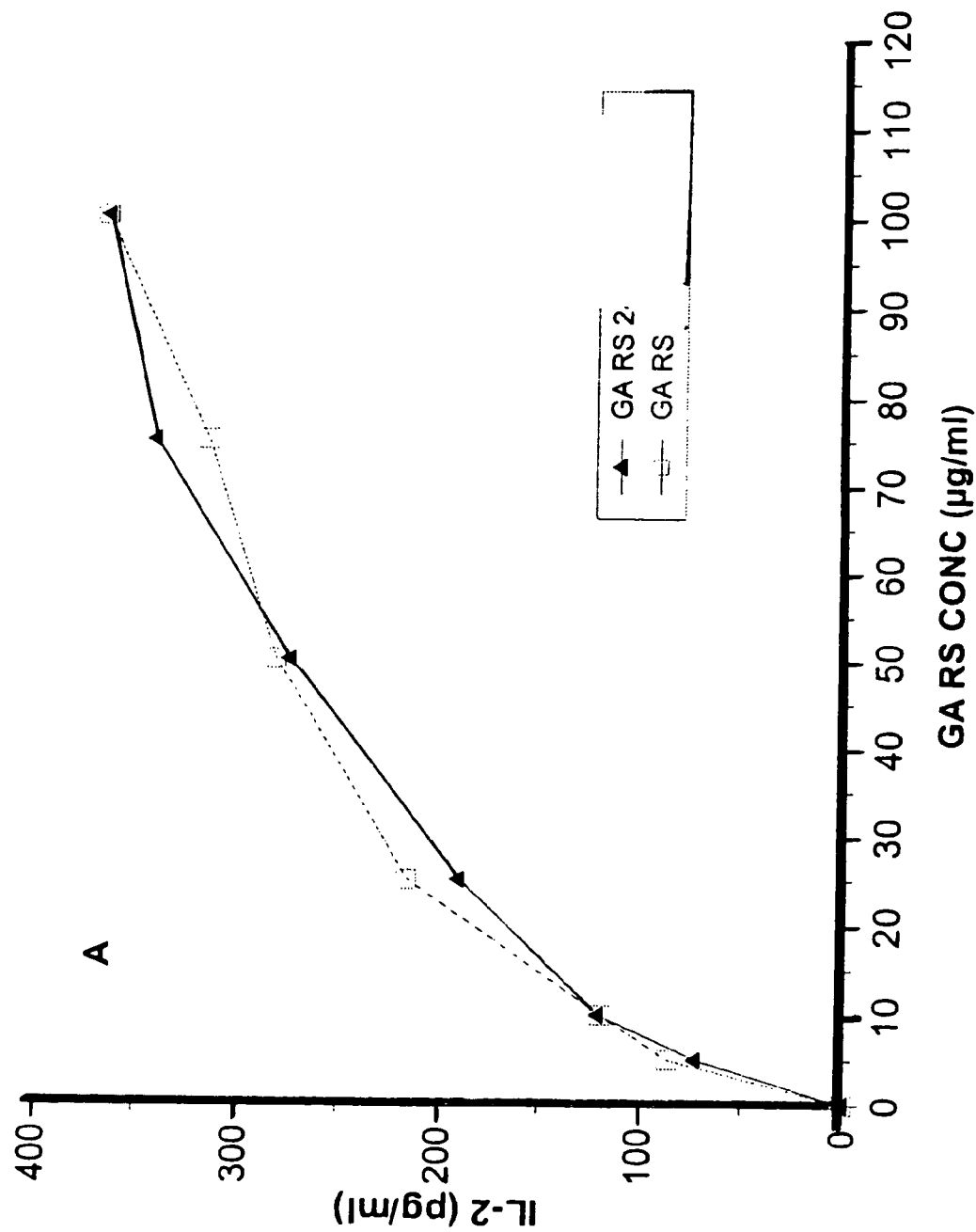
FIG. 12(A & B): Cross-reactivity of GA RS-specific T cells with GA DS and Drug Product (DP) batches. A primary culture of LN cells was prepared from mice immunized with 250 μg GA RS+CFA. The response of the GA RS-specific T cells to another GA DS batch (FIG. 12A), to a GA DP batch and to mannitol (FIG. 12B) was compared to the response to the GA RS batch. IL-2 levels in the culture media were measured by ELISA.
Figure 12B:
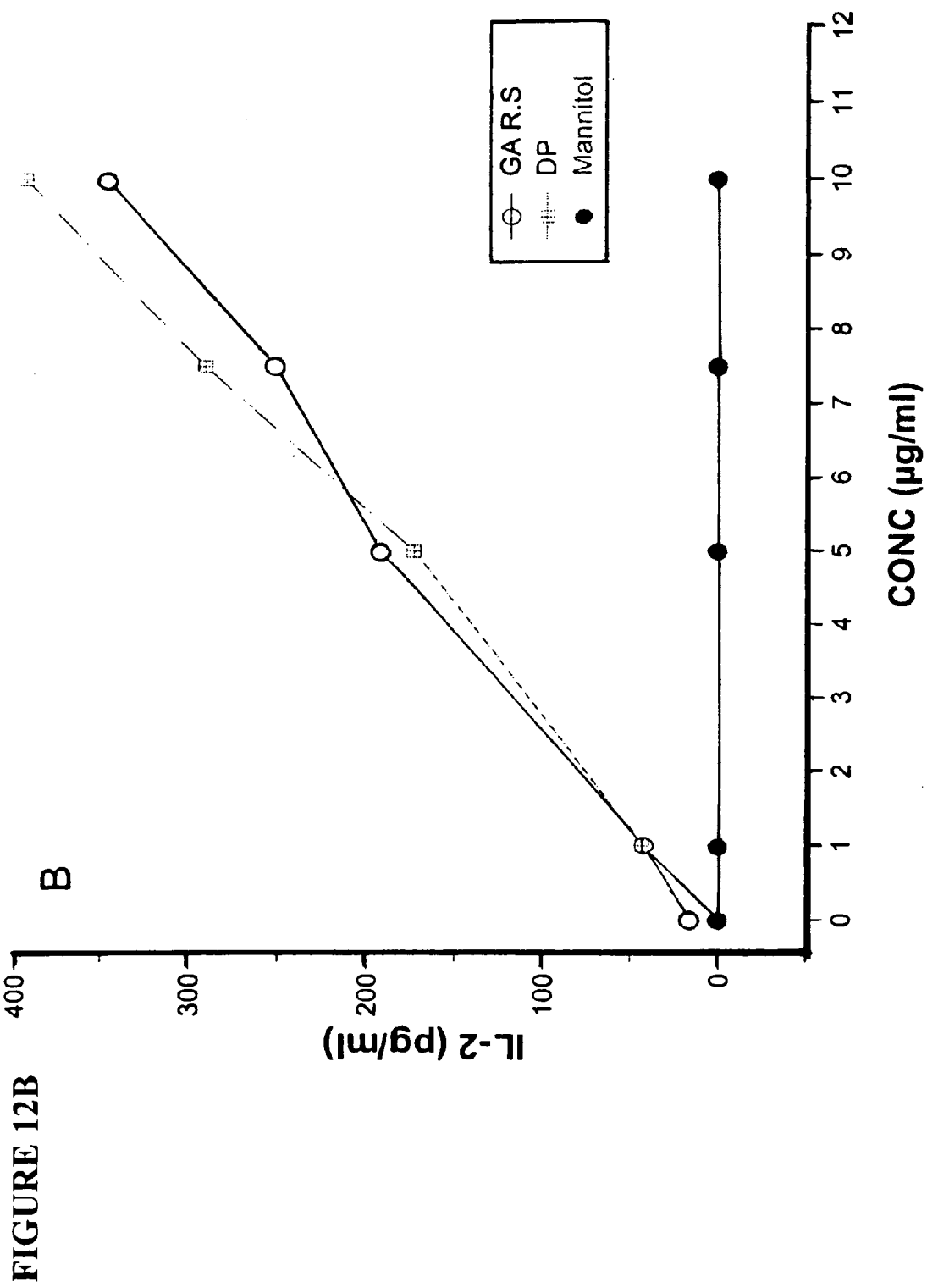

IL-2 was measured as in Experiment 3G(i). FIG. 12A shows that the LN cells cross-reacted with both standard batches. The dose-response curves of IL-2 secretion (measured by ELISA as above) by both batches were similar, indicating that the tested batches shared similar T-cell epitopes. Comparison between GA RS and a Copaxone® batch shows that the GA RS-specific T cells also cross-reacted with the DP batch, and that mannitol, the excipient in the Copaxone® formulation, did not affect or interfere with the T-cell responses (FIG. 12B). Thus, this method provides an indication of batch-to-batch reproducibility.

v) Discrimination Between GA and Related Copolymers

In Experiment 3G(ii), it was demonstrated that the in vitro test was sensitive to the average MW of GA peptides, using GA DS batches differing in their average MW. Since the experiment was based on bio-recognition of GA by GA-specific T cells, which specifically respond to linear sequences, it was expected that the method would be sensitive to variations/modifications in the sequences of GA peptides. This was demonstrated by using: 1) copolymers synthesized from only 3 out of the 4 amino acids comprising GA; 2) a GA batch (XX) resulting from deliberate modification in manufacturing conditions, i.e., addition of excess of free amino acids to GA monomers during synthesis. The average MW of this batch was high and out of specifications (MW=11150 Da); and 3) degradation products of GA RS obtained by proteolysis with trypsin and chymotrypsin.

Table 10 shows that the GA-specific T-cells did not respond to the 3 amino acid copolymers lacking lysine, alanine or tyrosine. In addition, the % response of the cells to the batch XX was relatively high and out of the method specifications (100±30%), indicating that the method might be sensitive to modifications in the production process. The high % response can also be explained by the sensitivity of the test to the MW of GA peptides, as demonstrated.

TABLE 10

Method Specificity

| Copolymer | Modification | Average % Potency ± RSD |
|---|---|---|
| Tyr-Lys-Glu | Lacking Alanine | 0 |
| Tyr-Ala-Glu | Lacking Lysine | 0 |
| Ala-Glu-Lys | Lacking Tyrosine | 0 |
| Batch XX | Excess of free amino acids in polymerization stage | 170 ± 4.7 |

Figure 13:
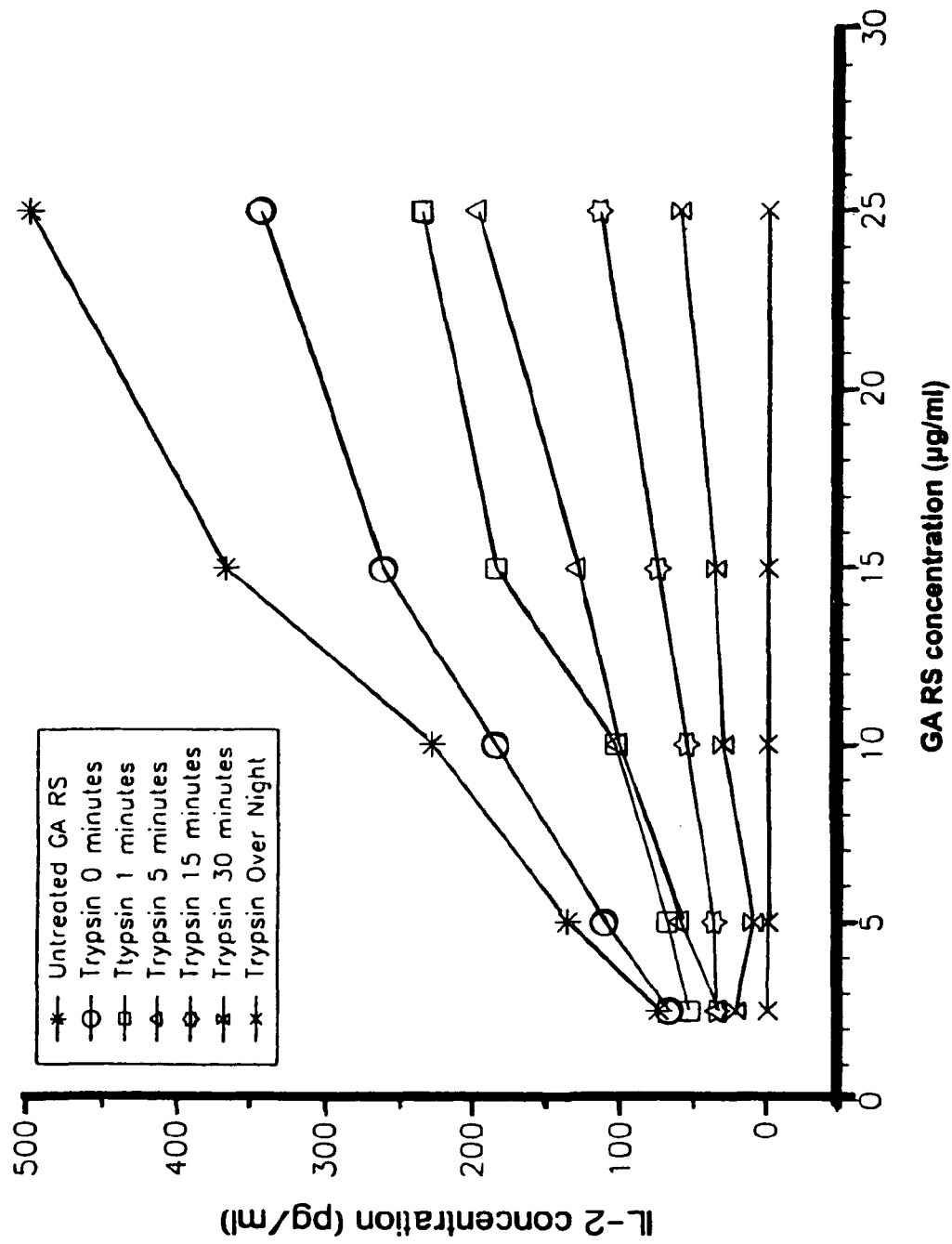
FIG. 13: Kinetics of GA RS proteolysis by trypsin. GA RS was proteolysed by trypsin for the indicated time points. The activity of the proteolysed samples was tested by the in vitro potency test.
Figure 14:
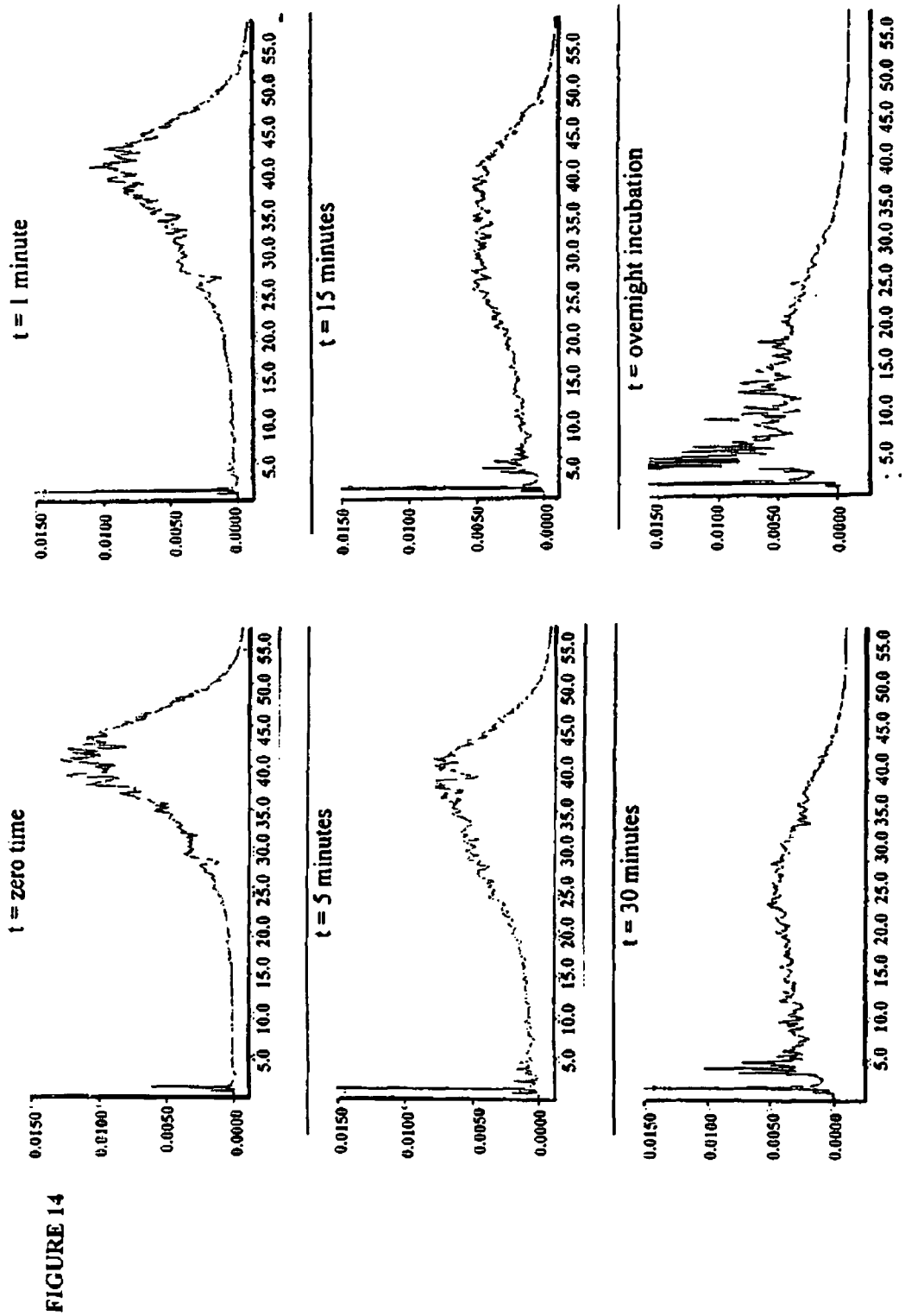
FIG. 14: Reverse-Phase High Pressure Liquid Chromatography (RP-HPLC) of GA before and after proteolysis by trypsin. GA RS was proteolysed by trypsin and the chromatographic profile of the samples was tested by RP-HPLC.
Figure 15:
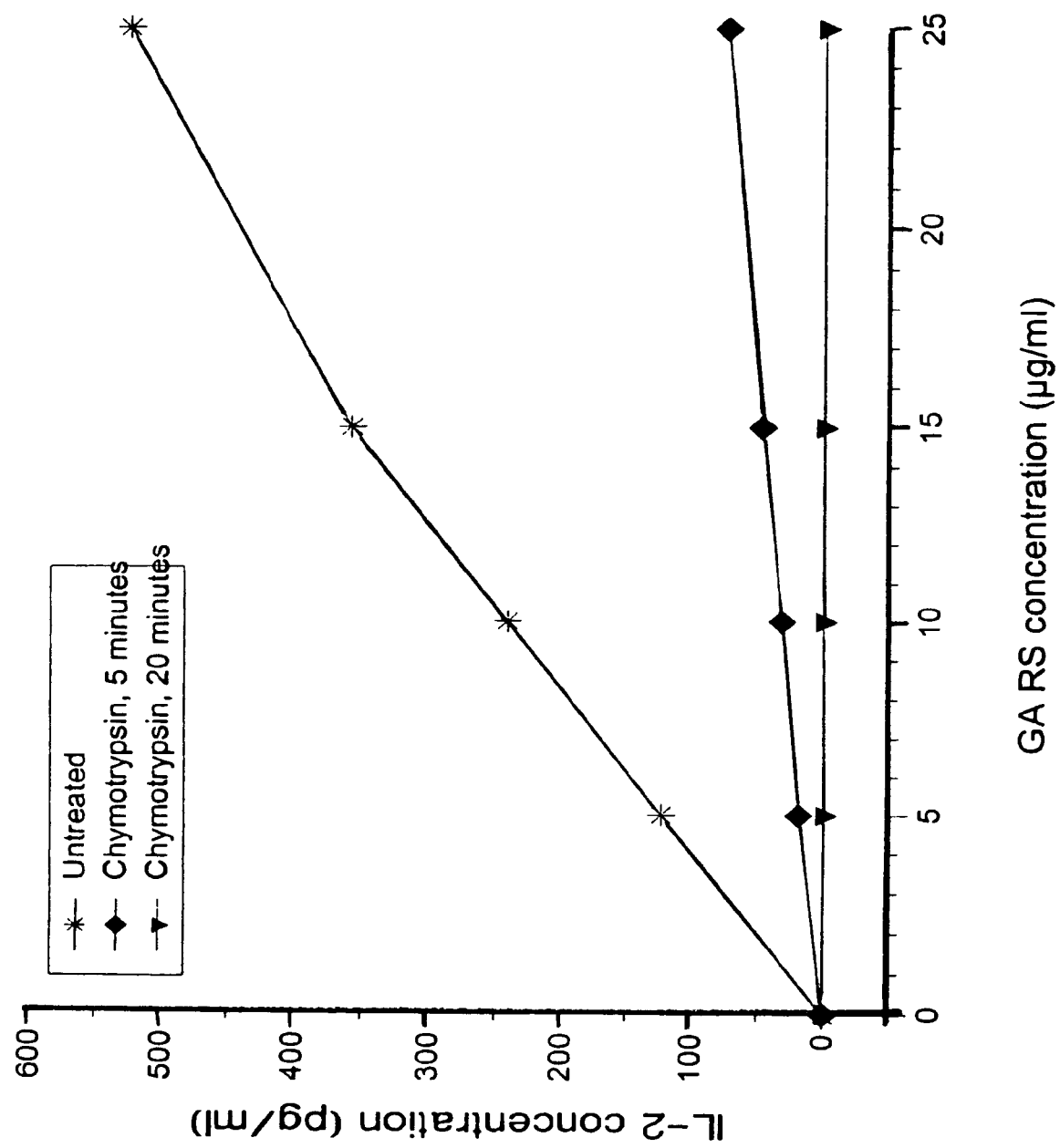
FIG. 15: Kinetics of GA RS proteolysis by chymotrypsin. GA RS was proteolysed by chymotrypsin for the indicated time points. The activity of the proteolysed samples was tested by the in vitro potency test.
Figure 16:
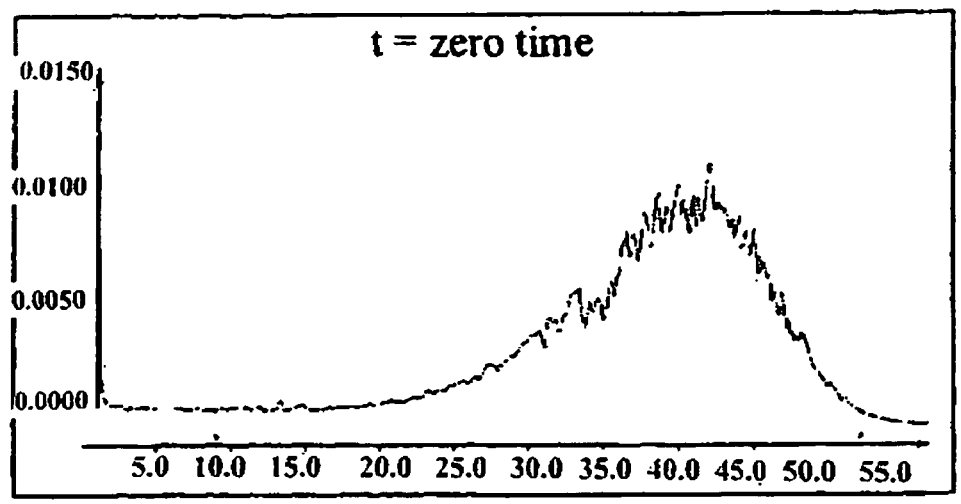
FIG. 16: RP-HPLC of GA before and after proteolysis by chymotrypsin. GA RS was proteolysed by chymotrypsin and the chromatographic profile of the samples was tested by RP-HPLC.
Figure 16:
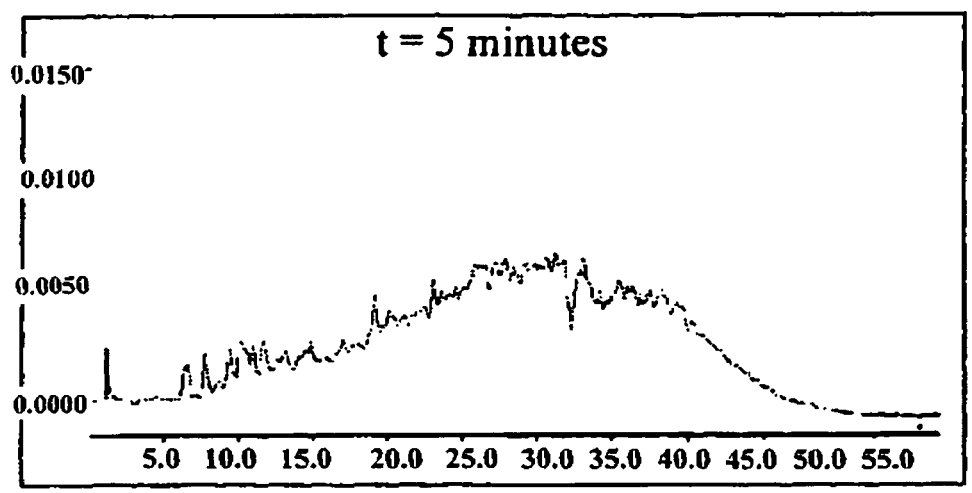
Figure 16:
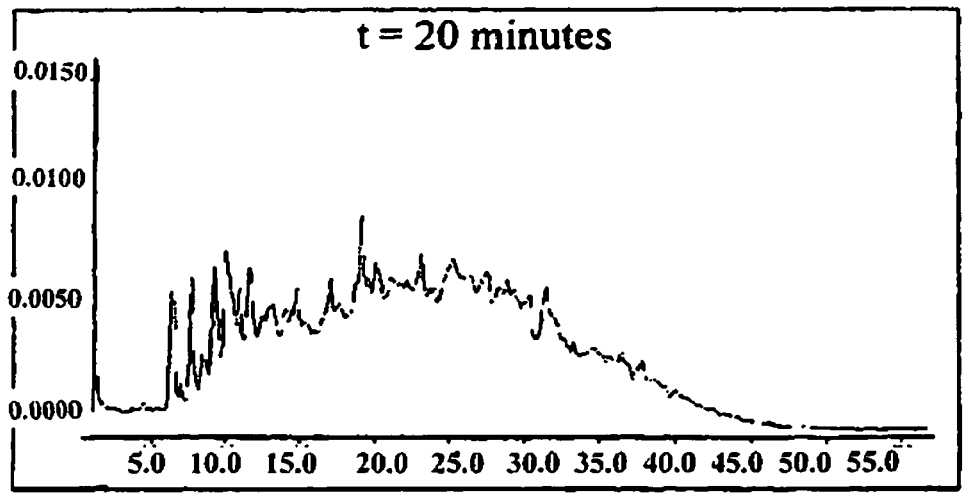

Kinetics studies of GA RS proteolysis by trypsin and chymotrypsin show that the in vitro test was sensitive to degradation of GA peptides. FIGS. 13 and 15 show that the secretion of IL-2 by the cells was reduced upon proteolysis time, and the % potency of the cells to the proteolysed peptides was out of the method specifications (100±30%) (Table 11). Overlay chromatograms (by RP-HPLC) of the degraded samples (FIGS. 14 and 16) demonstrated the kinetics of the proteolysis by trypsin and chymotrypsin, respectively. The cumulative results from all specificity studies revealed that the method was highly specific to GA and discriminated between GA and closely related antigens.

TABLE 11

Method Specificity - Effect of Proteolysis

| Enzyme | Time of proteolysis (minutes) | Average % Potency |
|---|---|---|
| Trypsin | 1 | 40 |
|  | 5 | 36 |
|  | 15 | 19 |
|  | 30 | 7 |
|  | overnight | 0 |
| Chymotrypsin | 5 | 11 |
|  | 20 | 0 |

Experiment 3G: Robustness i) Robustness of Acceptance Criteria

The consistency and robustness of the defined acceptance criteria was examined by comparing the resulting estimates of the relative potency obtained for the repeated GA batches. The batch analysis data included a number of repeated GA batches. Two batches were measured on three different days by different operators. One batch was tested on two different days by different operators, as well.

In the parallelism test for the repeated GA batches, all GA batch slopes values were within the appropriate critical limits for the parallelism slope ratio test. All GA batches satisfied the acceptance criteria for the point estimates of the relative potency values with 95% fiducial limits (the estimated % potency was within the limits of 80%-125% and the 95% fiducial limits were within the range of 70%-143%). For the analyzed data of the repeated GA batches, their validity did not depend on the day of experiment or the operator performing the test. This data supports the robustness of established specifications.

ii) Robustness of Critical Parameters in the Immunization Procedure and the In Vitro Reaction The robustness of critical parameters in both the immunization procedure and the in vitro reaction was evaluated. Briefly, it was shown that: 1) the immunological response of the LN cells was not affected by the immunizing dose of GA RS; 2) the immunization period was 9-11 days; 3) the response of the LN cells to GA RS was higher compared to the spleen cells response; 4) immunization with GA RS+CFA resulted in the LN cells having a stronger response compared to immunization with ICFA; 5) the presence of serum in culture media strongly affected the GA-specific T cell response, thus the in vitro reaction was performed in a serum-free media; 6) the optimal time frame for collecting the culture media was 18-21 hours following incubation with GA RS and test samples; and 7) the culture media can be kept at $-20°$C. for up to one week before tested in ELISA. Thus, it was shown that the method was robust.

Summary Statistics for the Point Estimate and 95% Fiducial Limits of Relative Potency
95% Tolerance Limits for the Mean Relative Potency To assess the acceptance limits for the estimated relative potency of a new batch, the mean and the standard deviation of the individual log(potency) estimates were calculated:

Mean($M_i$)=0.0074;

SD($M_i$)=0.0402.

An approximated 95% tolerance range for the mean relative potency value, based on the analyzed data, was:

$[10^{Mean(M_i) \pm 2 \cdot SD(M_i)}] \cdot 100\% = [84\%, 122\%]$.

Range of the 95% Fiducial Limits of Relative Potency

The minimum and maximum values of the 95% Fiducial Limits for the individual relative potency estimates were:

Minimum(Low Limit)=79.3%

Maximum(High Limit)=147.3%

Satisfaction of the Acceptance Criteria

Based on the analysis, the acceptance criteria were determined to be:
1. The assumptions involved in bioassay analysis approach were fulfilled, namely:
   a. Independence and normality of the log(responses);
   b. Homogeneity of the variance of the log(responses);
   c. No outliers; and
   d. Parallelism (non-significance of the slope ratio test).
2. The estimated relative potency was not less than 80% and not more than 125% of the standard potency; and
3. The 95% Fiducial Limits of error of the estimated relative potency were not less than 70% and not more than 143% of the standard potency.

Discussion of Example 3

Validation of the in vitro test revealed that the method was reproducible and the mean accuracy and precision were in an acceptable range. The method was highly specific to GA peptides and sensitive to the quality of the active substance.

SUMMARY AND DISCUSSION

An in vitro method was developed for GA DS and Copaxone® batches. This method was based on bio-recognition of T-cell epitopes (linear sequences) by GA RS-specific T cells. The GA RS-specific T cells secrete Th$_0$ cytokines in response to GA in culture. In this method, the recognition of GA batches by T cells is monitored by measuring the levels of IL-2 in the culture media by ELISA. It was shown that the GA RS-specific T cells are cross-reactive with both DS and DP batches, indicating that these batches share similar sequences with the RS batch, and that mannitol, the excipient in the DP formulation, does not interfere with the reaction.

The method was very specific to GA peptides and is sensitive to the average MW of the peptide mixture. MBP was not recognized by the GA-specific T cells. MBP immunodominant peptides (both encephalitogenic and suppressive peptides), as well as single peptides with amino-acid composition similar to that of GA, did not stimulate the T cells. Critical parameters in the immunization procedure, as well as in the in-vitro reaction, were optimized during this experiment. This experiment showed that the method was very reproducible and robust.

The method can be adapted to standardize other T cell antigens for use in pharmaceutical compositions. A primary culture of T cells specific to an antigen RS, instead of GA RS, can be made from animals immunized against the antigen RS. The cytokine production of this culture in response to antigen RS and in response to the sample antigen can be measured. The cytokine production in response to antigen RS can be plotted against the concentration of antigen RS to create a standard curve. The cytokine production in response to the sample antigen can be compared to the standard curve to determine whether the antigen is within the acceptable range of potency.

The optimum cytokine to monitor can be determined as in Experiment 2A. Conditions for immunization and the in vitro test may be optimized as in Experiments 2B and C.

REFERENCES

U.S. Pat. No. 3,849,550, issued Nov. 19, 1974 (Teitelbaum, et al.).
U.S. Pat. No. 5,800,808, issued Sep. 1, 1998 (Konfino, et al.).
PCT International Publication No. WO 00/05250, published Feb. 3, 2000 (Aharoni et al.).
PCT International Publication No. WO 00/18794
Aharoni, R. et al., T suppressor hybridomas and interleukin-2-dependent lines induced by copolymer 1 or by spinal cord homogenate down-regulate experimental allergic encephalomyelitis, Eur. J. Immunol., (1993), 23: 17-25.
Bornstein, et al., New Eng. J. Med., 1987, 317(7), 408-414.
Johnson, K. P., Neurology, 1:65-70 (1995).
Lando et al., Effect of cyclophosphamide on suppressor cell activity in mice unresponsive to EAE, J. Immunol. (1979) 123(5): 2156-2160.
Lisak et al., In vitro and in-vivo immune responses to homologous myelin basic protein in EAE, Cell. Immunol. (1974) 11:212-220. "Copaxone" in *Physician's Desk Reference*, 2000, Medical Economics Co., Inc., Montvale, N.J., 3115.
"Validation of Analytical Procedures: Methodology", November 1996 (CPMP/ICH/281/95).
European Pharmacopoeia, 1997.

What is claimed:
1. A process for measuring the potency of a test batch of glatiramer acetate relative to the known potency of a reference standard batch which comprises
   a) immunizing female (SJLXBALB/C)F1 mice between 8 and 12 weeks of age with a predetermined amount of glatiramer acetate from the reference standard batch;
   b) preparing a primary culture of T-cells from the mice of step (a) 9-11 days after immunization;

c) separately incubating at least five reference samples, each of which contains a predetermined number of cells from the primary culture of step (b) and a predetermined amount of glatiramer acetate between 1 µg/ml and 25 µg/ml from a reference standard batch;

d) incubating at least two samples, each of which contains a predetermined number of cells from the primary culture of step (b) and a predetermined amount of glatiramer acetate from the test batch;

e) determining for each sample in steps (c) and (d), the amount of interleukin-2 secreted by the cells in each sample after 18-21 hours of incubation of such sample;

f) correlating the amounts of interleukin-2 secreted by the samples incubated with the test batch of glatiramer acetate with the amounts of interleukin-2 secreted by the samples incubated with the reference standard batch of glatiramer acetate so as to determine the potency of the test batch of glatiramer acetate relative to the reference standard batch of glatiramer acetate, wherein in each sample in steps (c) and (d), the predetermined number of cells is substantially identical, and wherein for each sample containing a predetermined amount of glatiramer acetate from the test batch there is a corresponding reference sample containing a substantially identical predetermined amount of glatiramer acetate from the reference standard batch.

2. The process of claim 1, wherein six reference samples are separately incubated in step (c).

3. A process for measuring the potency of a test batch of glatiramer acetate relative to the known potency of a reference standard batch which comprises a) immunizing a test mammal with a predetermined amount of glatiramer acetate from the reference standard batch;

b) preparing a primary culture of T-cells from the test mammal of step (a) at a predetermined time after immunization;

c) separately incubating at least two reference samples, each of which contains a predetermined number of cells from the primary culture of step (b) and a predetermined amount of glatiramer acetate from a reference standard batch;

d) incubating at least two samples, each of which contains a predetermined number of cells from the primary culture of step (b) and a predetermined amount of glatiramer acetate from the test batch;

e) determining for each sample in steps (c) and (d), the amount of a cytokine secreted by the cells in each sample after a predetermined time period of incubation of such sample;

f) correlating the amounts of the cytokine secreted by the samples incubated with the test batch of glatiramer acetate with the amounts of the cytokine secreted by the samples incubated with the reference standard batch of glatiramer acetate so as to determine the potency of the test batch of glatiramer acetate relative to the reference standard batch of glatiramer acetate, wherein in each sample in steps (c) and (d), the predetermined number of cells is substantially identical, and wherein for each sample containing a predetermined amount of glatiramer acetate from the test batch there is a corresponding reference sample containing a substantially identical predetermined amount of glatiramer acetate from the reference standard batch.

4. The process of claim 3, wherein the cytokine is an interleukin.

5. The process of claim 4, wherein the interleukin is interleukin-2.

6. The process of claim 4, wherein the interleukin is interleukin-6.

7. The process of claim 4, wherein the interleukin is interleukin-10.

8. The process of claim 3, wherein the cytokine is interferon-gamma.

9. The process of claim 3, wherein the mammal is a rodent.

10. The process of claim 9, wherein the rodent is a mouse.

11. The process of claim 10, wherein the mouse is a female (SJLXBALB/C)F1 mouse.

12. The process of claim 3, wherein the mammal is about 8 to about 12 weeks old.

13. The process of claim 3, wherein the cells are lymph node cells.

14. The process of claim 3, wherein the cells are spleen cells.

15. A process for preparing a batch of glatiramer acetate as acceptable for pharmaceutical use which comprises
a) preparing a batch of glatiramer acetate;
b) measuring the relative potency of the batch according to the process of claim 1; and
c) qualifying the batch as acceptable for pharmaceutical use if the relative potency so measured is between 80% and 125% of the reference standard batch of glatiramer acetate.

16. A process for preparing glatiramer acetate acceptable for pharmaceutical use which comprises
a) preparing a batch of glatiramer acetate;
b) measuring the relative potency of the batch according to the process of claim 3; and
c) qualifying the batch as acceptable for pharmaceutical use if the relative potency so measured is between 80% and 125% of the reference standard batch of glatiramer acetate.

17. A process for preparing a pharmaceutical composition comprising glatiramer acetate, the process comprising
a) preparing a batch of glatiramer acetate to be tested;
b) measuring the potency of the batch of glatiramer acetate relative to the potency of a reference standard batch of glatiramer acetate by a process comprising:
i) immunizing female (SJLXBALB/C)F1 mice between 8 and 12 weeks of age with a predetermined amount of glatiramer acetate from the reference standard batch;
ii) preparing a primary culture of T-cells from the immunized mice of step (i);
iii) separately incubating at least five reference samples, each of which contains a predetermined number of cells from the primary culture of step (ii) and a predetermined amount of glatiramer acetate between 1 µg/ml and 25 µg/ml from the reference standard batch;
iv) incubating at least two samples, each of which contains a predetermined number of cells from the primary culture of step (ii) and a predetermined amount of glatiramer acetate from the batch of glatiramer acetate;
v) determining for each sample in steps (iii) and (iv), the amount of interleukin-2 secreted by the cells in each sample after 18-21 hours of incubation of such sample;
vi) correlating the amounts of interleukin-2 secreted by the samples incubated with the batch of glatiramer acetate with the amounts of interleukin-2 secreted by the samples incubated with the reference standard batch of glatiramer acetate so as to determine the potency of the test batch of glatiramer acetate relative to the reference standard batch of glatiramer acetate, wherein in each sample in steps (iii) and (iv), the predetermined number of cells is substantially identical, and wherein for each sample containing a predetermined amount of glatiramer acetate from the batch of glatiramer acetate there is a corresponding reference sample containing a substantially identical predetermined amount of glatiramer acetate from the reference standard batch; and c) preparing the pharmaceutical composition using the batch of glatiramer acetate if the relative potency of the batch of glatiramer acetate is between 80% and 125% of the potency of the reference standard batch.

18. The process of claim 17, wherein six reference samples are separately incubated in step (b).

19. A process for preparing a pharmaceutical composition comprising glatiramer acetate, the process comprising a) preparing a batch of glatiramer acetate to be tested;

b) measuring the potency of the batch of glatiramer acetate relative to the potency of a reference standard batch of glatiramer acetate by a process comprising:

i) immunizing a test mammal with a predetermined amount of glatiramer acetate from the reference standard batch;

ii) preparing a primary culture of T-cells from the test mammal of step (i) at a predetermined time after immunization;

iii) separately incubating at least two reference samples, each of which contains a predetermined number of cells from the primary culture of step (ii) and a predetermined amount of glatiramer acetate from the reference standard batch;

iv) incubating at least two samples, each of which contains a predetermined number of cells from the primary culture of step (ii) and a predetermined amount of glatiramer acetate from the batch of glatiramer acetate;

v) determining for each sample in steps (iii) and (iv), the amount of a cytokine secreted by the cells in each sample after a predetermined time period of incubation of such sample;

vi) correlating the amounts of the cytokine secreted by the samples incubated with the batch of glatiramer acetate with the amounts of the cytokine secreted by the samples incubated with the reference standard batch of glatiramer acetate so as to determine the potency of the batch of glatiramer acetate relative to the reference standard batch of glatiramer acetate, wherein in each sample in steps (iii) and (iv), the predetermined number of cells is substantially identical, and wherein for each sample containing a predetermined amount of glatiramer acetate from the batch there is a corresponding reference sample containing a substantially identical predetermined amount of glatiramer acetate from the reference standard batch; and c) preparing the pharmaceutical composition using the batch of glatiramer acetate if the relative potency of the batch of glatiramer acetate is between 80% and 125% of the potency of the reference standard batch.

20. The process of claim 19, wherein the cytokine is an interleukin.

21. The process of claim 20, wherein the interleukin is interleukin-2.

22. The process of claim 20, wherein the interleukin is interleukin-6.

23. The process of claim 20, wherein the interleukin is interleukin-10.

24. The process of claim 19, wherein the cytokine is interferon-gamma.

25. The process of claim 19, wherein the mammal is a rodent.

26. The process of claim 25, wherein the rodent is a mouse.

27. The process of claim 26, wherein the mouse is a female (SJLXBALB/C)F1 mouse.

28. The process of claim 27, wherein the cells are lymph node cells.

29. The process of claim 27, wherein the cells are spleen cells.

30. The process of claim 19, wherein the mammal is about 8 to about 12 weeks old.

* * * * *